United States Patent
Nadgoud et al.

(10) Patent No.: US 10,301,353 B2
(45) Date of Patent: May 28, 2019

(54) CO-CRYSTAL OF CARFILZOMIB WITH MALEIC ACID AND PROCESS FOR THE PREPARATION OF PURE CARFILZOMIB

(71) Applicant: DR. REDDY'S LABORATORIES LIMITED, Hyderabad (IN)

(72) Inventors: Ramesh Kumar Nadgoud, Hyderabad (IN); Sridhar Vasam, Warangal (IN); Siva Reddy Makireddy, Guntur (IN); Veerender Murki, Hyderabad (IN); Rakesh Ganorkar, Hyderabad (IN); Jithin Jose, Kottayam (IN); Subba Reddy Peddi Reddy, Hyderabad (IN); Praveen Chappa, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 15/540,459

(22) PCT Filed: Dec. 31, 2015

(86) PCT No.: PCT/IB2015/060064
§ 371 (c)(1),
(2) Date: Jun. 28, 2017

(87) PCT Pub. No.: WO2016/108204
PCT Pub. Date: Jul. 7, 2016

(65) Prior Publication Data
US 2017/0369528 A1   Dec. 28, 2017

(30) Foreign Application Priority Data
Dec. 31, 2014   (IN) .......................... 6852/CHE/2014

(51) Int. Cl.
*A61K 38/00* (2006.01)
*C07K 5/103* (2006.01)
*C07C 51/43* (2006.01)
*C07C 57/145* (2006.01)
*C07K 1/30* (2006.01)

(52) U.S. Cl.
CPC ............ *C07K 5/1008* (2013.01); *C07C 51/43* (2013.01); *C07C 57/145* (2013.01); *C07K 1/306* (2013.01)

(58) Field of Classification Search
None
See application file for complete search history.

(56) References Cited

U.S. PATENT DOCUMENTS

| 7,417,042 B2 | 8/2008 | Smyth et al. |
| 7,927,613 B2 | 4/2011 | Almarsson et al. |
| 8,207,125 B2 | 6/2012 | Smyth et al. |
| 8,921,324 B2 | 12/2014 | Phiasivongsa et al. |

OTHER PUBLICATIONS

International Search Report dated May 30, 2016, for corresponding International Patent Application No. PCT/IB2015/060064.
Written Opinion dated May 30, 2016, for corresponding International Patent Application No. PCT/IB2015/060064.
International Preliminary Report on Patentability dated Jul. 4, 2017, for corresponding International Patent Application No. PCT/IB2015/060064.
Berenson et al., "Replacement of bortezomib with carfilzomib for multiple myeloma patients progressing from bortezomib combination therapy", Leukemia, Feb. 7, 2014, pp. 1529 to 1536, vol. 28, Macmillan Publishers Limited.

*Primary Examiner* — Jeanette M Lieb
(74) *Attorney, Agent, or Firm* — Pergament & Cepeda LLP; Milagros A. Cepeda; Edward D. Pergament

(57) ABSTRACT

Aspects of the present application relates to co-crystal of carfilzomib with maleic acid, process for the preparation of co-crystal of carfilzomib with maleic acid, process for the preparation of pure carfilzomib from co-crystal of carfilzomib with maleic acid and process for the preparation of amorphous carfilzomib.

13 Claims, 3 Drawing Sheets

CO-CRYSTAL OF CARFILZOMIB WITH MALEIC ACID AND PROCESS FOR THE PREPARATION OF PURE CARFILZOMIB

This application is a National Stage Application under 35 U.S.C. § 371 of PCT International Application No. PCT/IB2015/060064, filed Dec. 31, 2015, which claims the benefit of Indian Provisional Application No. 6852/CHE/2014, filed Dec. 31, 2014, all of which are hereby incorporated by references in their entireties.

Aspects of the present application relates to co-crystal of carfilzomib with maleic acid, process for the preparation of co-crystal of carfilzomib with maleic acid, process for the preparation of pure carfilzomib from co-crystal of carfilzomib with maleic acid and process for the preparation of amorphous carfilzomib.

Carfilzomib is a tetrapeptide epoxyketone proteasome inhibitor that irreversibly binds to the N-terminal threonine-containing active sites of the 20S proteasome, the proteolytic core particle within the 26S proteasome. Carfilzomib had antiproliferative and proapoptotic activities in vitro in solid and hematologic tumor cells. In animals, carfilzomib inhibited proteasome activity in blood and tissue and delayed tumor growth in models of multiple myeloma, hematologic, and solid tumors.

The chemical name for carfilzomib is (2S)—N—((S)-1-((S)-4-methyl-1-((R)-2-methyloxiran-2-yl)-1-oxopentan-2-ylcarbamoyl)-2-phenylethyl)-2-((S)-2-(2-morpholino acetamido)-4-phenylbutanamido)-4-methylpentanamide. Carfilzomib has the following structure:

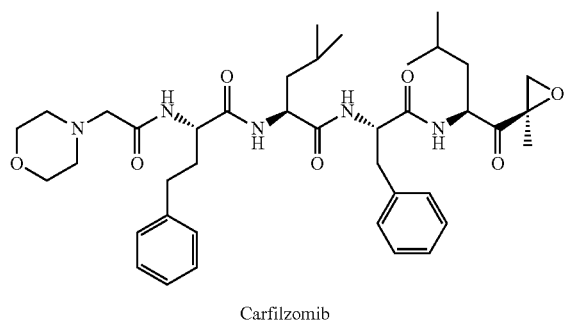 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

Carfilzomib

U.S. Pat. Nos. 7,417,042 and 8,207,125 specifically disclosed carfilzomib, its pharmaceutically acceptable salts and its pharmaceutical composition.

U.S. Pat. No. 8,207,297 discloses process for the preparation of carfilzomib or a pharmaceutically acceptable salt thereof. U.S. Pat. No. 8,367,617 describes crystalline carfilzomib. U.S. Pat. No. 8,921,324 describes process for the preparation of citrate salt of carfilzomib.

Process for the purification of carfilzomib through formation of co-crystal of carfilzomib with maleic acid is particularly unexpected for the reason that the generally employed method for purifying carfilzomib by crystallization. The process for the purification of carfilzomib through the formation of co-crystal of carfilzomib with maleic acid avoids the column chromatography and repeated recrystallization to get the desired purity.

Though, there are processes for the purification of carfilzomib available in the literature still there remains a need of process which is environmentally-friendly, cost effective and industrially applicable.

SUMMARY OF THE INVENTION

In an aspect, the present invention relates to co-crystal of carfilzomib with maleic acid.

In an aspect, the present invention relates to co-crystal of carfilzomib with maleic acid characterized by peaks in the powder x-ray diffraction pattern at 2θ values of 7.4±0.2, 18.1±0.2 and 18.7±0.2. Co-crystal of carfilzomib with maleic acid further characterized by peaks in the powder x-ray diffraction pattern at 2θ values of 4.5±0.2, 9.2±0.2, 16.3±0.2, 20.2±0.2, 20.6±0.2, 21.7±0.2 and 22.3±0.2.

In an aspect, the present invention relates to co-crystal of carfilzomib with maleic acid having powder x-ray diffraction pattern as shown in FIG. 2.

In an aspect, the present invention provides process for the preparation of co-crystal of carfilzomib with maleic acid comprising:
a) preparing a solution of carfilzomib in a solvent;
b) adding maleic acid;
c) isolating co-crystal of carfilzomib with maleic acid.

In an aspect, the present invention provides a process for the preparation of pure carfilzomib comprising:
a) preparing co-crystal of carfilzomib with maleic acid;
b) optionally, purifying co-crystal of carfilzomib with maleic acid;
c) converting the co-crystal of carfilzomib with maleic acid to carfilzomib free-base;
d) optionally, purifying carfilzomib.

In an aspect, the present invention provides a process for the preparation of pure carfilzomib comprising:
a) treating lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one and adding maleic acid to provide co-crystal of carfilzomib with maleic acid;
b) optionally, purifying the co-crystal of carfilzomib with maleic acid using solvent;
c) converting the co-crystal of carfilzomib with maleic acid to carfilzomib free-base using base;
d) isolating the pure carfilzomib;
e) optionally, further purifying carfilzomib.

In an aspect, the present invention provides a process for the preparation of amorphous carfilzomib comprising:
a) preparing a solution of carfilzomib in a solvent;
b) optionally, combining the solution of step a) with suitable antisolvent
c) isolating the amorphous carfilzomib.

In an aspect, the present invention provides a process for the preparation of amorphous carfilzomib comprising:
a) preparing a solution of carfilzomib in a solvent;
b) optionally, combining the solution of step a) with suitable antisolvent
c) isolating the amorphous carfilzomib.
wherein the solvent is selected from methanol, dichloromethane and anti-solvent is selected from water and n-heptane.

In an aspect, the present invention provides a process for the preparation of amorphous carfilzomib comprising:
a) preparing a solution of carfilzomib in methanol;
b) isolating the amorphous carfilzomib.

In an aspect, the present invention provides a HPLC method for analysing carfilzomib, wherein the mobile phase comprises first liquid A and a second liquid B, and the relative concentration of the liquids is varied to a predetermined gradient.

In an aspect, the present invention also provides pharmaceutical formulations comprising amorphous carfilzomib produced according to the process described herein together with one or more pharmaceutically acceptable excipients.

DETAILED DESCRIPTION

In an aspect, the present invention relates to co-crystal of carfilzomib with maleic acid.

In an aspect, the present invention relates to co-crystal of carfilzomib with maleic acid characterized by peaks in the powder x-ray diffraction pattern at 2θ values of 7.4±0.2, 18.1±0.2 and 18.7±0.2. Co-crystal of carfilzomib with maleic acid further characterized by peaks in the powder x-ray diffraction pattern at 2θ values of 4.5±0.2, 9.2±0.2, 16.3±0.2, 20.2±0.2, 20.6±0.2, 21.7±0.2 and 22.3±0.2.

Figure 2:
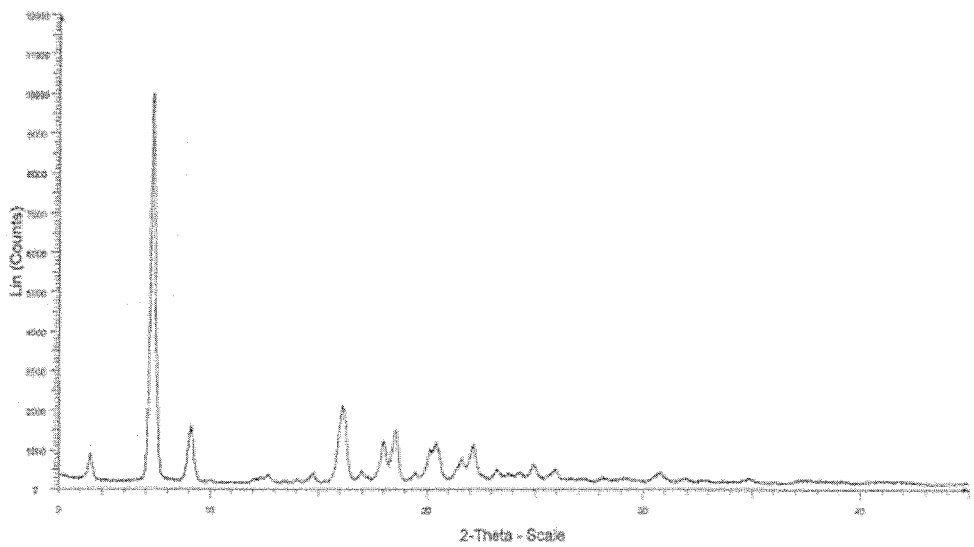
FIG. 2 illustrates an X-ray powder diffraction pattern of the co-crystal of carfilzomib with maleic acid, obtained according to the procedure of example 7.
Figure 3:
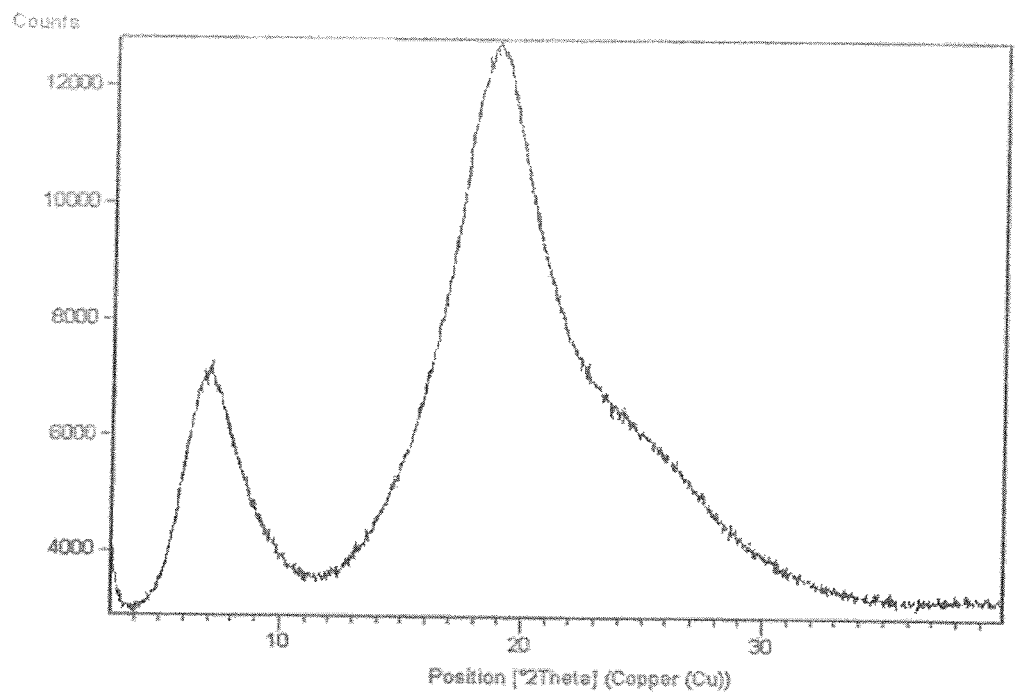
FIG. 3 illustrates an X-ray powder diffraction pattern of amorphous carfilzomib, obtained according to the procedure of example 17.

In an aspect, the present invention relates to co-crystal of carfilzomib with maleic acid having powder x-ray diffraction pattern as shown in FIG. 2

The co-crystal of carfilzomib with maleic acid is further characterized by the unit cell parameters by PXRD, DSC and TGA, the details are mentioned here under.

Figure 5:
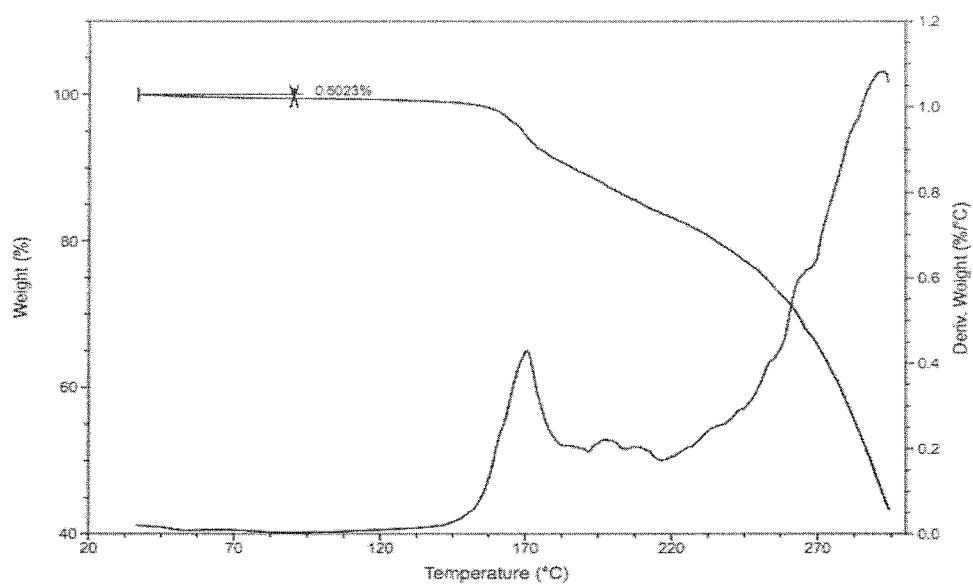
FIG. 5 shows a thermogravimetric analysis (TGA) curve of the co-crystal of carfilzomib with maleic acid.

Thermal gravimetric analysis (TGA) experiments were performed on TA Instruments model Q500. The sample (about 10-30 mg) was placed in a platinum pan previously tared. The weight loss of the sample was determined by heating the sample from room temperature to 300° C. at a heating rate of 10° C./min under nitrogen atmosphere of 40 mL/min. The weight loss of maleic acid co-crystal of carfilzomib was found to be 0.5% w/w and the corresponding thermogram was shown in FIG. 5.

Figure 4:
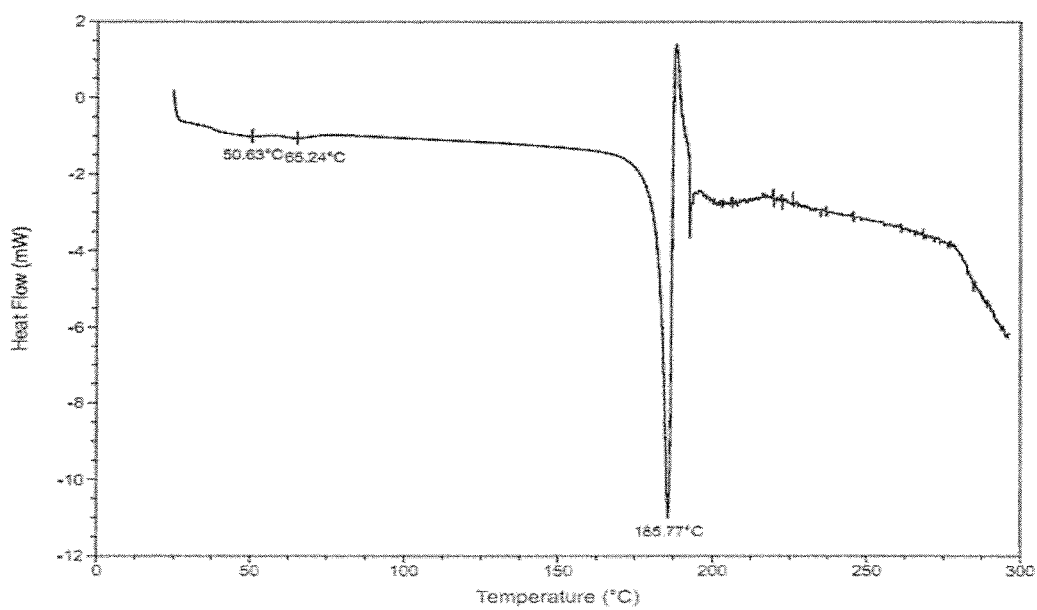
FIG. 4 shows a differential scanning calorimetry (DSC) thermogram of the co-crystal of carfilzomib with maleic acid.

The thermal analysis of maleic acid co-crystal of carfilzomib was carried out by differential scanning calorimetry (DSC) (TA Instruments-Q1000) equipped with refrigerated cooling accessory. Analysis was performed by taking 3 to 7 mg of sample encapsulated into aluminum sample pan with pierced lid. The thermogram was recorded from 25° C. to 300° C. under nitrogen atmosphere of 50 mL/min at a heating rate of 10° C./min. A sharp endothermic event of maleic acid co-crystal of carfilzomib was observed at a peak maximum temperature of 186° C. followed by decomposition. The corresponding thermogram was shown in FIG. 4.

Powder X-ray diffraction (PXRD) data reported herein was obtained by a Bruker AXS D8 Advance Powder X-ray Diffractometer with Lynxeye detector and Copper anode (wavelength 1.5418 Å). The diffraction profile was collected using following setting parameters of the diffractometer: the X-Ray tube was operated at a voltage of 40 kV and current of 40 mA; Ni filtered Cu Kα1 radiation (λ=1.5418 Å); scan type—continuous mode; scan range (2θ) 3° to 45°; step size 0.013° 2θ; time per step 0.1 sec. The representative diffractogram was depicted in FIG. 2.

TABLE 1

| | Lattice parameters | | | | | | | | |
|---|---|---|---|---|---|---|---|---|---|
| T | a (Å) | b (Å) | c (Å) | α° | β° | γ° | V(Å$^3$) | Z' | SG |
| 25 | 19.790(5) | 9.807(8) | 12.067(7) | 90 | 98.117(9)° | 90 | 2318 | 1 | P2$_1$ |

T = temp (° C.) for the crystallographic data.
Z' = number of drug molecules per asymmetric unit
V = unit cell volume
SG = space group The stoichiometric ratio between the carfilzomib and maleic acid in the maleic acid co-crystal of carfilzomib may be in the range of 3:1 to 1:3. According to present application the preferred and most suitable stoichiometric ratio is 1:1.

In an aspect, the present invention provides process for the preparation of co-crystal of carfilzomib with maleic acid comprising:
  a) preparing a solution of carfilzomib in a solvent;
  b) adding maleic acid;
  c) isolating co-crystal of carfilzomib with maleic acid.

In embodiments of step a), preparing a solution of carfilzomib in suitable solvents that may be used include, but are not limited to, ether solvent; nitrile solvents; alcohol solvents; halogenated hydrocarbon solvents; ester solvents; polar aprotic solvents; ketone solvents; or mixtures thereof.

In embodiments of step a), preparing a solution of carfilzomib includes:
  i) direct use of a reaction mixture containing carfilzomib that is obtained in the course of its synthesis; or
  ii) dissolving carfilzomib in a solvent.

The dissolution temperatures may range from about 20° C. to about the reflux temperature of the solvent, depending on the solvent used for dissolution, as long as a clear solution of carfilzomib is obtained without affecting its quality.

In embodiments of step b), the maleic acid can be added as solid or maleic acid can be added in the form of solution by dissolving in solvents which are mentioned under step a).

In embodiments of step b), the maleic acid or maleic acid solution may be added to the carfilzomib solution obtained in step a) or vice-versa.

In embodiments of step b), the reaction mass is maintained at the temperature ranging between −15° C. to about 50° C. for about 15 minutes to about 6 hours, or longer for isolating the co-crystal of carfilzomib with maleic acid.

In embodiments of step c), the isolation may be done using techniques such as direct filtration or by scraping, or by shaking the container, removal of the solvent include using a rotational distillation device such as a buchi rotavapor, spray drying, agitated thin film drying, freeze drying (lyophilization), and the like, or other techniques specific to the equipment used. Small quantity of solvent or anti solvent may be added to the reaction flask or the reactor to make the slurry or suspension when the solvent is completely removed, which will be useful for easy filtration.

The solvent may be removed, optionally under reduced pressures, at temperatures less than reflux temperature of the solvent, less than about 100° C., less than about 60° C., less than about 40° C., less than about 20° C., or any other suitable temperatures.

The product thus isolated may be optionally further dried to afford co-crystal of carfilzomib with maleic acid.

Drying may be suitably carried out in a tray dryer, vacuum oven, buchi rotavapor, air oven, fluidized bed dryer, spin flash dryer, flash dryer, or the like. The drying may be carried out at atmospheric pressure or under reduced pressures at temperatures of less than about 100° C., less than about 60° C., less than about 40° C. or any other suitable temperatures. The drying may be carried out for any time period required for obtaining a desired quality, such as from about 15 minutes to several hours.

The compound obtained in step c), purifying by any of the procedures known in the art which include but not limited to recrystallization, slurry washing, purification through column chromatography etc. The solvents that can be used for the purification of co-crystal of carfilzomib with maleic acid may be selected from alcohol solvents; ether solvent; nitrile solvents; halogenated hydrocarbon solvents; ester solvents; polar aprotic solvents; ketone solvents; or mixtures thereof.

In an aspect, the present invention provides a process for the preparation of pure carfilzomib comprising:
a) preparing co-crystal of carfilzomib with maleic acid;
b) optionally, purifying co-crystal of carfilzomib with maleic acid;
c) converting the co-crystal of carfilzomib with maleic acid to Carfilzomib free-base;
d) optionally, purifying carfilzomib.

In embodiments of step a), preparing co-crystal of carfilzomib with maleic acid in suitable solvents that may be used include, but are not limited to, ether solvent; nitrile solvents; alcohol solvents; halogenated hydrocarbon solvents; ester solvents; polar aprotic solvents; ketone solvents; or mixtures thereof.

In specific embodiments of step a), preparing co-crystal of carfilzomib with maleic acid in suitable solvents that may be used include, but are not limited to ethyl acetate, DMF, water or mixtures thereof.

In embodiments of step b), purifying the co-crystal of carfilzomib with maleic acid can be done by any of the procedures known in the art which include but not limited to recrystallization, slurry washing, purification through column chromatography etc. The solvents that can be used for the purification of co-crystal of carfilzomib with maleic acid may be selected from alcohol solvents; ether solvent; nitrile solvents; halogenated hydrocarbon solvents; ester solvents; polar aprotic solvents; ketone solvents; or mixtures thereof.

In specific embodiment suitable solvents that may be used in step b), purifying the co-crystal of carfilzomib with maleic acid using suitable solvents that may be used include, but are not limited to DMF, acetonitrile and mixture thereof.

In embodiments of step c), converting the co-crystal of carfilzomib with maleic acid to free-base in presence of a solvent and a base.

In embodiments of step c), converting the co-crystal of carfilzomib with maleic acid to free-base using suitable solvents that may be used include, but are not limited to alcohol solvents; ether solvent; nitrile solvents; halogenated hydrocarbon solvents; ester solvents; polar aprotic solvents; ketone solvents; or mixtures thereof.

In specific embodiments of step c), converting the co-crystal of carfilzomib with maleic acid to free-base using suitable solvents that may be used include, but are not limited to methanol, water and mixture thereof.

In embodiments of step c), the suitable bases that may be used include both inorganic and organic bases. Bases that can be used, but are not limited to hydroxides, carbonates, bicarbonates, oxides, carboxylates, or alkoxides of alkali or alkaline earth metals such as sodium hydroxide, potassium hydroxide, sodium carbonate, potassium carbonate, sodium bicarbonate, or potassium bicarbonate, primary, secondary, and tertiary amines, such as ammonia, triethylamine, diisopropylethylamine, diisopropylamine, N-methyl morpholine and pyridine.

In specific embodiments, the suitable base that may be used in step c) is NaHCO$_3$ solution.

In embodiments of step c), suitable base that may be used 1 to 40 equivalents or more for 1 equivalent of co-crystal of carfilzomib with maleic acid.

In specific embodiments of step c), suitable base that may be used 15 equivalents for 1 equivalent of co-crystal of carfilzomib with maleic acid.

In embodiments of step c), the solution of co-crystal of carfilzomib with maleic acid may be added to the aqueous base solution or vice-versa.

In embodiments of step d), optionally further purifying carfilzomib using suitable solvents that may be used include, but are not limited to alcohol solvents; ether solvent; nitrile solvents; halogenated hydrocarbon solvents; ester solvents; polar aprotic solvents; ketone solvents; water or mixtures thereof.

In specific embodiments of step d), optionally further purifying carfilzomib using suitable solvents that may be used include, but are not limited to methanol, water or mixture thereof.

The product obtained in step d), dried to afford carfilzomib. Drying may be suitably carried out in a tray dryer, vacuum oven, buchi rotavapor, air oven, fluidized bed dryer, spin flash dryer, flash dryer, or the like. The drying may be carried out at atmospheric pressure or under reduced pressures at temperatures of less than about 100° C., less than about 60° C., less than about 40° C. or any other suitable temperatures. The drying may be carried out for any time period required for obtaining a desired quality, such as from about 15 minutes to several hours.

In an aspect, the present invention provides a process for the preparation of pure carfilzomib comprising:
a) treating lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one and adding maleic acid to provide co-crystal of carfilzomib with maleic acid;
b) optionally, purifying the co-crystal of carfilzomib with maleic acid using solvent;
c) converting the co-crystal of carfilzomib with maleic acid to carfilzomib free-base using base;
d) isolating the pure carfilzomib;
e) optionally, further purifying carfilzomib.

In embodiments of step a), preparing a co-crystal of carfilzomib with maleic acid by treating lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one and adding maleic acid.

In embodiments of step a) contain two steps:
(i) preparing carfilzomib by treating lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one in presence of a solvent and coupling reagent.

(ii) converting carfilzomib to co-crystal of carfilzomib with maleic acid.

In embodiments of step a), during the reaction between lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one, suitable solvents that may be used include, but are not limited to ester solvents; alcohol solvents; ether solvent; nitrile solvents; halogenated hydrocarbon solvents; polar aprotic solvents; ketone solvents; water or mixtures thereof.

In specific embodiments of step a), preparing carfilzomib in suitable solvents that may be used include, but are not limited to DMF, ethyl acetate, water or mixtures thereof.

In embodiments of step a), during the reaction between lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one, suitable coupling reagents that may be used include, but are not limited to N-hydroxyazabenzotriazole (HATU), dicyclohexylcarbodiimide (DCC), 1,3-diisopropylcarbodiimide (DIC), 1-(3-dimethylaminopropyl)-3-ethylcarbodiimide (EDC), carbonyldiimidazole and 1-hydroxybenzotriazole monohydrate (HOBT).

In embodiments of step a), preparing co-crystal of carfilzomib with maleic acid in suitable solvents that may be used include, but are not limited to, ether solvent; nitrile solvents; alcohol solvents; halogenated hydrocarbon solvents; ester solvents; polar aprotic solvents; ketone solvents; or mixtures thereof.

In specific embodiments of step a), preparing co-crystal of carfilzomib with maleic acid in suitable solvents that may be used include, but are not limited to ethyl acetate, DMF, water or mixtures thereof.

In embodiments of step b), purifying the co-crystal of carfilzomib with maleic acid can be done by any of the procedures known in the art which include but not limited to recrystallization, slurry washing, purification through column chromatography etc. The solvents that can be used for the purification of co-crystal of carfilzomib with maleic acid may be selected from alcohol solvents; ether solvent; nitrile solvents; halogenated hydrocarbon solvents; ester solvents; polar aprotic solvents; ketone solvents; or mixtures thereof.

In specific embodiments step b), purifying the co-crystal of carfilzomib with maleic acid using suitable solvents that may be used include, but are not limited to DMF, acetonitrile and mixture thereof.

In embodiments of step c), converting the co-crystal of carfilzomib with maleic acid to free-base in presence of a solvent and a base.

In embodiments of step c), converting the co-crystal of carfilzomib with maleic acid to free-base using suitable solvents that may be used include, but are not limited to alcohol solvents; ether solvent; nitrile solvents; halogenated hydrocarbon solvents; ester solvents; polar aprotic solvents; ketone solvents; water or mixtures thereof.

In specific embodiment step c), converting the co-crystal of carfilzomib with maleic acid to free-base using suitable solvents that may be used include, but are not limited to methanol, water and mixture thereof.

In embodiments of step c), the suitable bases that may be used include both inorganic and organic bases. Bases that can be used, but are not limited to hydroxides, carbonates, bicarbonates, oxides, carboxylates, or alkoxides of alkali or alkaline earth metals such as sodium hydroxide, potassium hydroxide, sodium carbonate, potassium carbonate, sodium bicarbonate, or potassium bicarbonate, primary, secondary, and tertiary amines, such as ammonia, triethylamine, diisopropylethylamine, diisopropylamine, N-methyl morpholine and pyridine.

In specific embodiment step c), the suitable bases that may be used include, but are not limited to NaHCO3.

In embodiments of step c), suitable base that may be used 1 to 40 equivalents or more for 1 equivalent of co-crystal of carfilzomib with maleic acid.

In specific embodiments of step c), suitable base that may be used 15 equivalents for 1 equivalent of co-crystal of carfilzomib with maleic acid.

In embodiments of step c), the solution of co-crystal of carfilzomib with maleic acid may be added to the aqueous base solution or vice-versa.

In one embodiment of step d), the isolation may be effected by combining the solution of step c) with a suitable anti-solvent. Adding the solution obtained in step c) to the anti-solvent, or adding an anti-solvent to the solution obtained in step c), to effect the crystallization process are both within the scope of the present invention. Optionally, the addition may be carried out after concentrating the solution obtained in step c). Suitable anti-solvents that may be used include, but are not limited to: water; hydrocarbon solvents, aqueous base or mixtures thereof.

Optionally, the isolation may be effected by removing the solvent. Suitable techniques which may be used for the removal of the solvent include using a rotational distillation device such as a buchi rotavapor, spray drying, agitated thin film drying, freeze drying (lyophilization), and the like, or any other suitable technique.

The compound obtained from step d), may be collected using techniques such as direct filtration or by scraping, or by shaking the container, or other techniques specific to the equipment used. Small quantity of solvent or anti solvent may be added to the reaction flask or the reactor to make the slurry or suspension when the solvent is completely removed, which will be useful for easy filtration.

The compound obtained from step d) optionally, further purifying carfilzomib using suitable solvents that may be used include, but are not limited to alcohol solvents; ether solvent; nitrile solvents; halogenated hydrocarbon solvents; ester solvents; polar aprotic solvents; ketone solvents; water or mixtures thereof.

In embodiments of step e), purification of carfilzomib can be done by any of the procedures known in the art which include but not limited to recrystallization, solvent and anti-solvent technic, slurry washing, purification through column chromatography etc. The solvent and anti-solvent that can be used for the purification of carfilzomib is methanol and water.

The product thus isolated may be optionally further dried to afford carfilzomib. Drying may be suitably carried out in a tray dryer, vacuum oven, buchi rotavapor, air oven, fluidized bed dryer, spin flash dryer, flash dryer, or the like. The drying may be carried out at atmospheric pressure or under reduced pressures at temperatures of less than about 100° C., less than about 60° C., less than about 40° C. or any other suitable temperatures. The drying may be carried out for any time period required for obtaining a desired quality, such as from about 15 minutes to several hours.

The dried product may be optionally milled to get desired particle sizes. Milling or micronization may be performed before drying, or after the completion of drying of the product. Techniques that may be used for particle size reduction include, without limitation, ball, roller and hammer mills, and jet mills. etc., to produce a desired particle size distribution. carfilzomib obtained according to certain processes of the present application has a particle size distribution wherein: d(0.5) is less than about 100 µm, or less than about 25 µm, or less than about 10 µm; and d(0.9) is less than about 200 µm, or less than about 50 µm, or less than about 30 µm. Particle size distributions can be determined using any means, including laser light diffraction equipment sold by Malvern Instruments limited, Malvern, Worcestershire, United Kingdom, Coulter counters, microscopic procedures, etc. The term d(x) means that a particular fraction has particles with a maximum size being the value given; 0.5 represents 50% of the particles and 0.9 represents 90% of the particles.

A specific process for the preparation of pure carfilzomib by a method of present application can be illustrated as given below in Scheme 1.

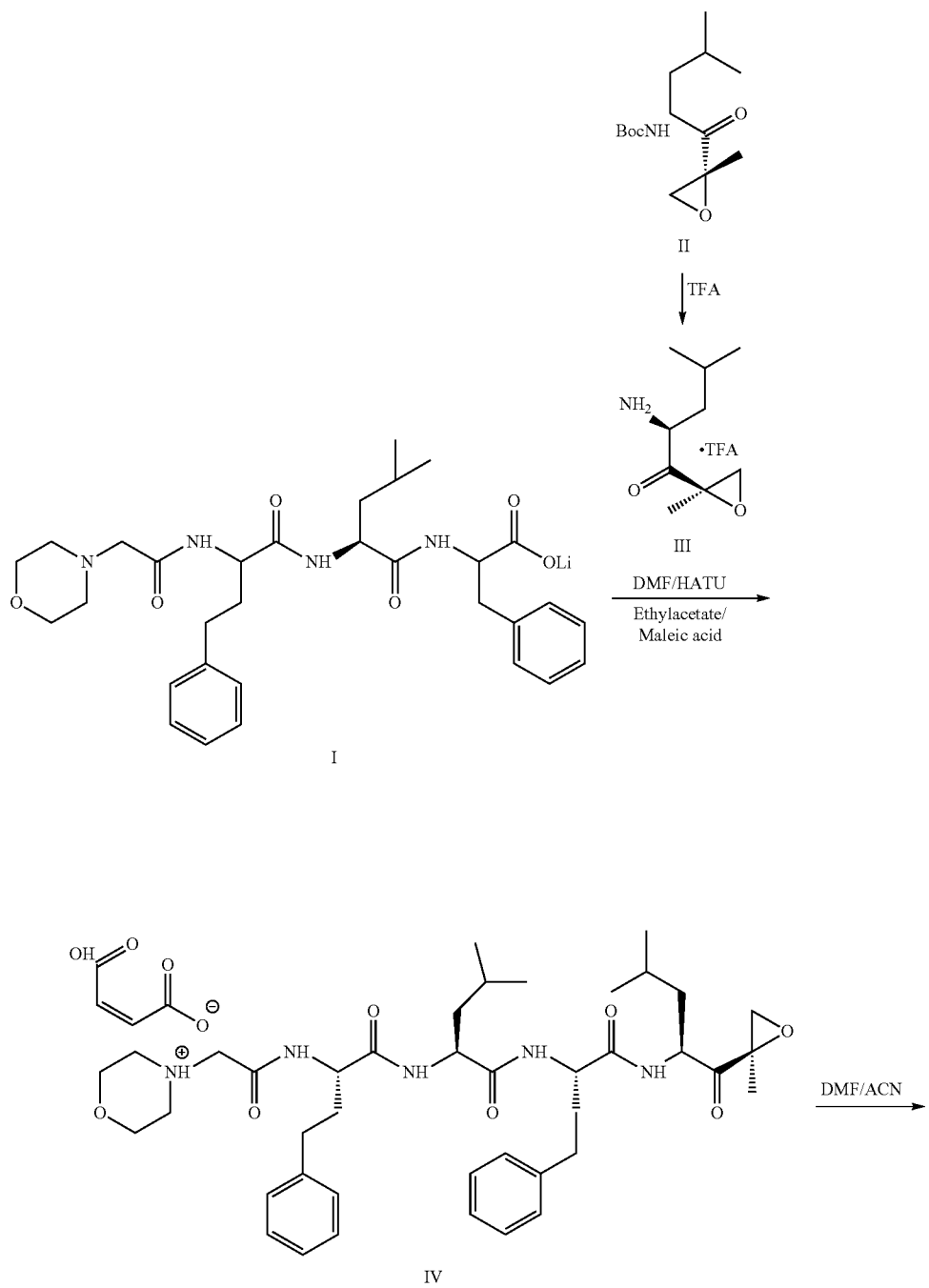

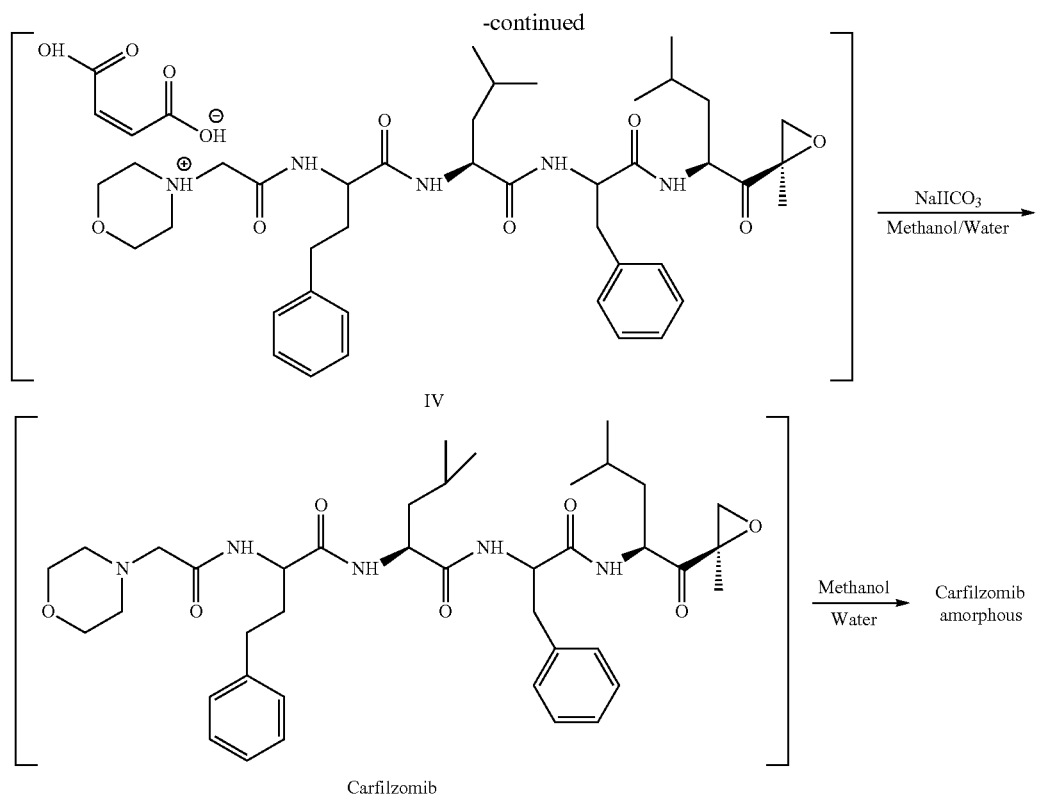
The starting material (I) of carfilzomib can be prepared by any known methods (or) the process can be illustrated as given below in Scheme 2.

Scheme 2
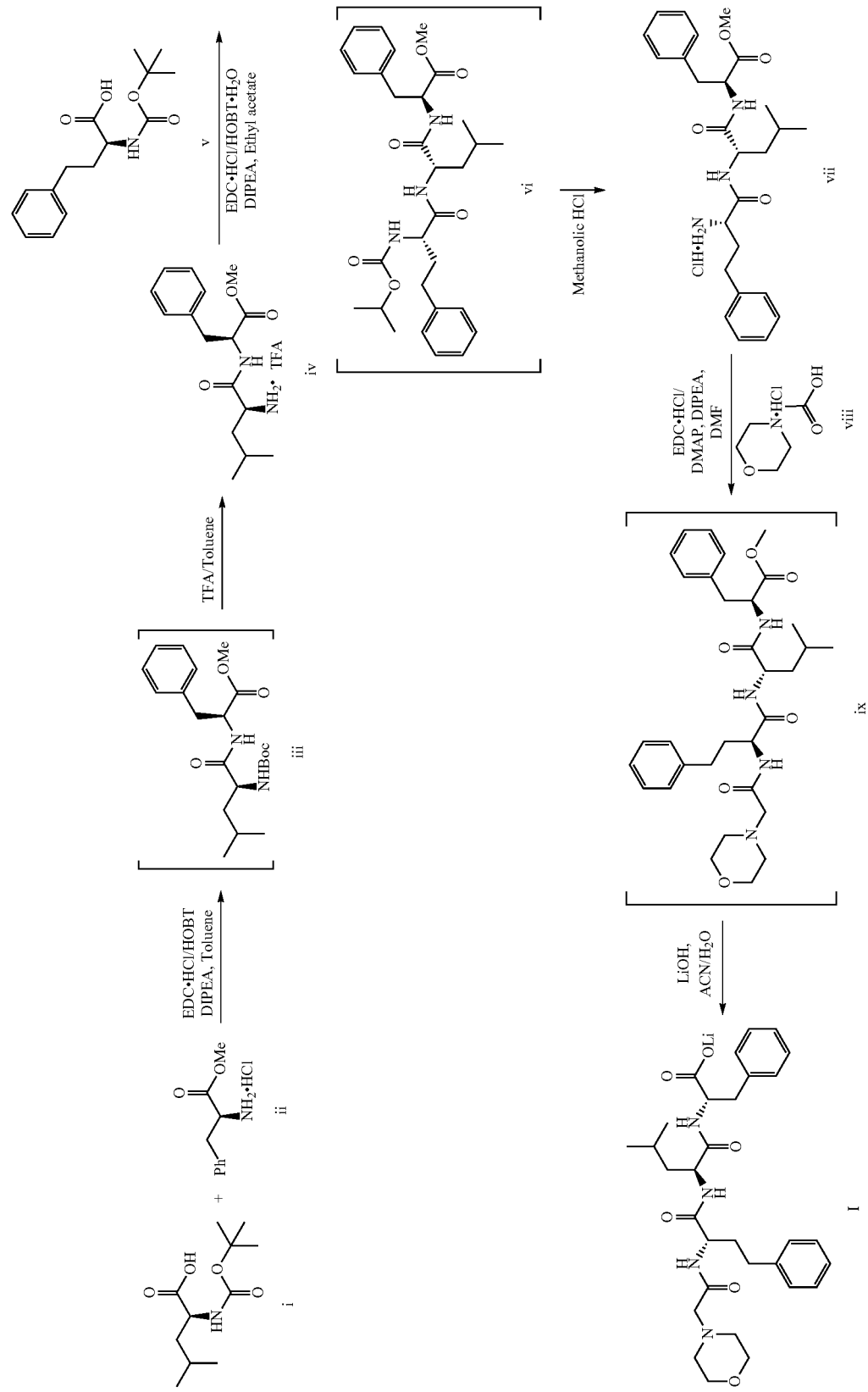

The starting material (II) of Carfilzomib can be prepared by any known methods.

In an aspect, the present invention provides a process for the preparation of amorphous carfilzomib comprising:
a) preparing a solution of carfilzomib in a solvent;
b) optionally, combining the solution of step a) with suitable antisolvent
c) isolating the amorphous carfilzomib.

In embodiments of step a), preparing a solution of carfilzomib includes:
i) direct use of a reaction mixture containing carfilzomib that is obtained in the course of its synthesis; or
ii) dissolving carfilzomib in a solvent.

Any physical form of carfilzomib may be utilized for providing the solution of carfilzomib in step a). Carfilzomib that may be used as the input for the process of the present invention may be obtained by any process including the processes described in the art. For example carfilzomib may be prepared by the process described in U.S. Pat. No. 7,417,042.

Suitable solvents that may be used in step a) include, but are not limited to, alcohol solvents; halogenated hydrocarbon solvents; ester solvents; nitrile solvents; polar aprotic solvents; ketone solvents; or mixtures thereof.

In specific embodiments suitable solvents that may be used in step a) is selected from methanol, dichloromethane or mixtures thereof.

The dissolution temperatures may range from about 20° C. to about the reflux temperature of the solvent, depending on the solvent and quantity used for dissolution. The solution may optionally be treated with carbon, flux-calcined diatomaceous earth (Hyflow), or any other suitable material to remove color and/or to clarify the solution.

Optionally, the solution obtained above may be filtered to remove any insoluble particles. The insoluble particles may be removed suitably by filtration, centrifugation, decantation, or any other suitable techniques. The solution may be filtered by passing through paper, glass fiber, or other membrane material, or a bed of a clarifying agent such as celite or hyflow. Depending upon the equipment used and the concentration and temperature of the solution, the filtration apparatus may need to be preheated to avoid premature crystallization.

In embodiments of step b), suitable antisolvents that may be used include, but are not limited to hydrocarbon solvents; water; or mixtures thereof.

In specific embodiments of step b), suitable antisolvents that may be used include, but are not limited to water, n-heptane or mixtures thereof.

In embodiments of step b), the isolation may be effected by combining the solution of step a) with a suitable anti-solvent. Adding the solution obtained in step a) to the anti-solvent, or adding an anti-solvent to the solution obtained in step a), to effect the crystallization process are both within the scope of the present invention. Optionally, the addition may be carried out after concentrating the solution obtained in step a). After adding anti-solvent, the reaction mass may be maintained from 15 minutes to 10 hours.

In embodiments of step c), the compound obtained from step b) may be collected using techniques such as direct filtration or by scraping, or by shaking the container, or other techniques specific to the equipment used. Small quantity of solvent or anti solvent may be added to the reaction flask or the reactor to make the slurry or suspension when the solvent is completely removed, which will be useful for easy filtration.

The product thus isolated may be optionally further dried to afford an amorphous form of carfilzomib.

Drying may be suitably carried out in a tray dryer, vacuum oven, buchi rotavapor, air oven, fluidized bed dryer, spin flash dryer, flash dryer, or the like. The drying may be carried out at atmospheric pressure or under reduced pressures at temperatures of less than about 100° C., less than about 60° C., less than about 40° C. or any other suitable temperatures. The drying may be carried out for any time period required for obtaining a desired quality, such as from about 15 minutes to several hours.

In an aspect, the present invention provides a process for the preparation of amorphous carfilzomib comprising:
a) preparing a solution of carfilzomib in a solvent;
b) optionally, combining the solution of step a) with suitable antisolvent
c) isolating the amorphous carfilzomib.
wherein the solvent is selected from methanol, dichloromethane and anti-solvent is selected from water and n-heptane.

Embodiments of process for the preparation of amorphous carfilzomib described above also applicable for this specific process for the preparation of amorphous carfilzomib.

In an aspect, the present invention provides a process for the preparation of amorphous carfilzomib comprising:
a) preparing a solution of carfilzomib in methanol;
b) isolating the amorphous carfilzomib.

In embodiments of step a) preparing a solution of carfilzomib includes:
i) direct use of a reaction mixture containing carfilzomib that is obtained in the course of its synthesis; or
ii) dissolving carfilzomib in methanol.

Any physical form of carfilzomib may be utilized for providing the solution of carfilzomib in step a). Carfilzomib that may be used as the input for the process of the present invention may be obtained by any process including the processes described in the art. For example carfilzomib may be prepared by the process described in U.S. Pat. No. 7,417,042.

The dissolution temperatures may range from about 20° C. to 64° C. temperature. The methanol solution may optionally be treated with carbon, flux-calcined diatomaceous earth (Hyflow), or any other suitable material to remove color and/or to clarify the solution.

Optionally, the methanol solution obtained above may be filtered to remove any insoluble particles. The insoluble particles may be removed suitably by filtration, centrifugation, decantation, or any other suitable techniques. The solution may be filtered by passing through paper, glass fiber, or other membrane material, or a bed of a clarifying agent such as celite or hyflow. Depending upon the equipment used and the concentration and temperature of the solution, the filtration apparatus may need to be preheated to avoid premature crystallization.

In embodiments of step b), the isolation may be effected by removing the methanol. Suitable techniques which may be used for the removal of the methanol include using a rotational distillation device such as a buchi rotavapor, spray drying, agitated thin film drying, freeze drying (lyophilization), and the like, or any other suitable technique.

The methanol may be removed, optionally under reduced pressures, at temperatures less than 64° C. temperature.

The product thus isolated may be optionally further dried to afford an amorphous form of carfilzomib.

Drying may be suitably carried out in a tray dryer, vacuum oven, buchi rotavapor, air oven, fluidized bed dryer, spin flash dryer, flash dryer, or the like. The drying may be carried out at atmospheric pressure or under reduced pressures at temperatures of less than about 100° C., less than about 60° C., less than about 40° C. or any other suitable temperatures. The drying may be carried out for any time period required for obtaining a desired quality, such as from about 15 minutes to several hours.

Figure 1:
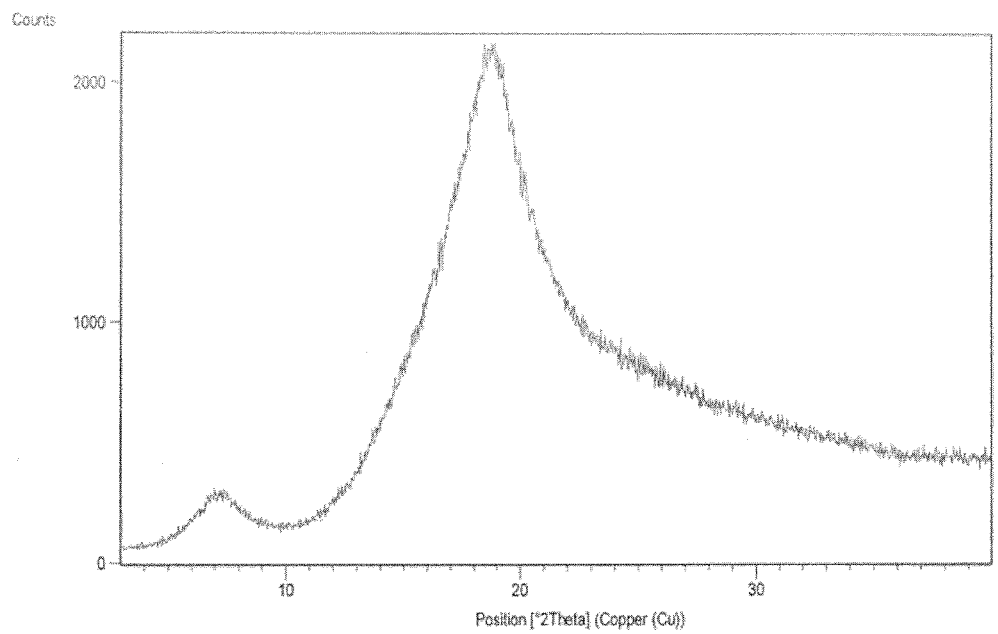
FIG. 1 illustrates an X-ray powder diffraction pattern of amorphous carfilzomib, obtained according to the procedure of example 2.

Examples of amorphous carfilzomib obtained using the above process is characterized by powder X-ray diffraction ("PXRD") pattern substantially as illustrated by FIG. 1

In an aspect, the present invention provides a process for the purification of carfilzomib comprising:
a) loading silicagel and carfilzomib into column;
b) eluting the carfilzomib from the column with solvent; and
c) isolating the pure carfilzomib from the eluant.

In embodiments of step a), suitable silicagel that may be used having particle size 60-120 mesh, 100-200 mesh, 200-400 mesh or 230-400 mesh.

In embodiments of step a), carfilzomib can be loaded into a column directly as a solid or making the solution or slurry using suitable solvents that may be used include, but are not limited to halogenated hydrocarbon solvent, ester solvent, alcohol solvent or mixture thereof.

In embodiments of step b), suitable solvents that may be used for elution from the column include, but are not limited to hydrocarbon solvents; ester solvents; ketone solvents; halogenated hydrocarbon solvent; alcohol solvent or mixtures thereof.

In embodiments of step c), the eluant obtained in step b) can be evaporated to isolate the pure carfilzomib using technique such as removal of the solvent include using a rotational distillation device such as a buchi rotavapor, spray drying, agitated thin film drying, freeze drying (lyophilization), and the like, or other techniques specific to the equipment used.

The solvent may be removed, optionally under reduced pressures, at temperatures less than reflux temperature of the solvent, less than about 100° C., less than about 60° C., less than about 40° C., less than about 20° C., or any other suitable temperatures. The product thus isolated may be optionally further dried to afford carfilzomib.

Drying may be suitably carried out in a tray dryer, vacuum oven, buchi rotavapor, air oven, fluidized bed dryer, spin flash dryer, flash dryer, or the like. The drying may be carried out at atmospheric pressure or under reduced pressures at temperatures of less than about 100° C., less than about 60° C., less than about 40° C. or any other suitable temperatures. The drying may be carried out for any time period required for obtaining a desired quality, such as from about 15 minutes to several hours.

The starting carfilzomib before loading silica-gel column may contain purity of less than 95%. The purity of the carfilzomib obtained after the treatment with silicagel column increase the HPLC purity 1% to 20% from the initial loaded carfilzomib purity. The same operation can be repeated to further increase the purity of the carfilzomib (or) it can be purified through recrystallization (or) by the process described in this application.

In an aspect of the application, carfilzomib produced by a method of present application can be chemically pure carfilzomib having purity greater than about 99.5% and containing no single impurity in amounts greater than about 0.15%, by HPLC.

Potential Impurities possible in carfilzomib, described in the present application, can have formulas as illustrated below.

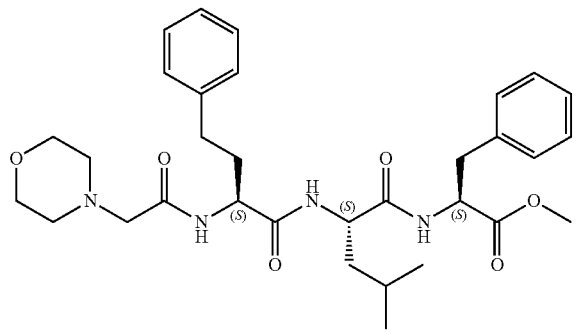

Methyl((S)-2-(2-morpholinoacetamido)-4-phenylbutanoyl)-L-leucyl-L-phenyl alaninate

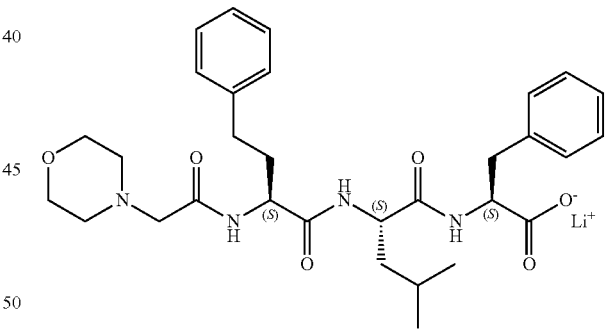

Lithium((S)-2-(2-morpholinoacetamido)-4-phenylbutanoyl)-L-leucyl-L-phenyl alaninate

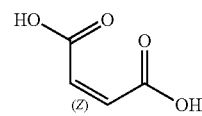

Maleic Acid

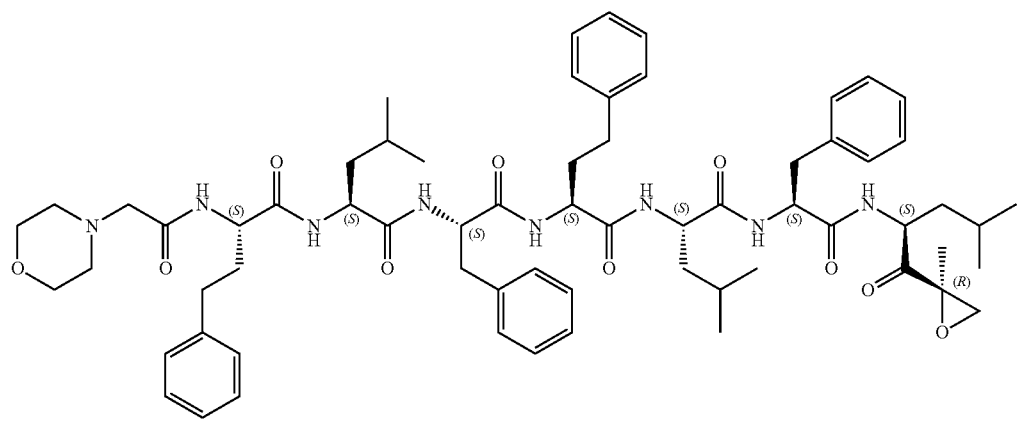

(S)-2-((2S,5S,8S,11S)-5-benzyl-8-isobutyl-14-morpholino-4,7,10,13-tetraoxo-2,11-diphenethyl-3,6,9,12-tetraazatetradecanamido)-4-methyl-N—((S)-1-(((S)-4-methyl-1-((R)-2-methyloxiran-2-yl)-1-oxopentan-2-yl)amino)-1-oxo-3-phenylpropan-2-yl) pentan amide

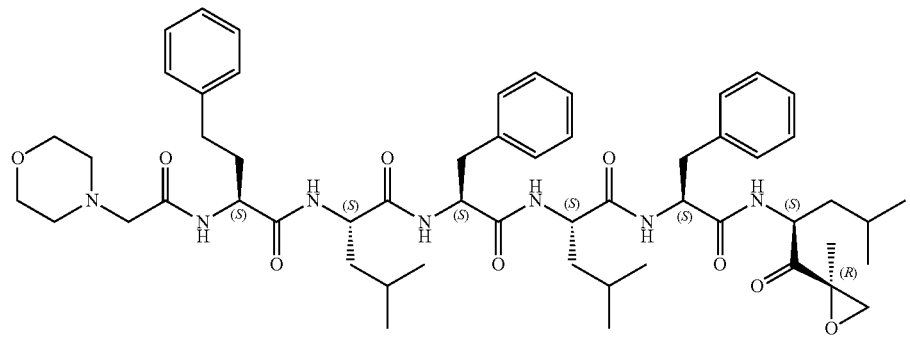

(S)-4-methyl-N—((S)-1-(((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)amino)-1-oxo-3-phenylpropan-2-yl)-2-((S)-2-(2-morpholinoacetamido)-4-phenylbutanamido) pentanamide

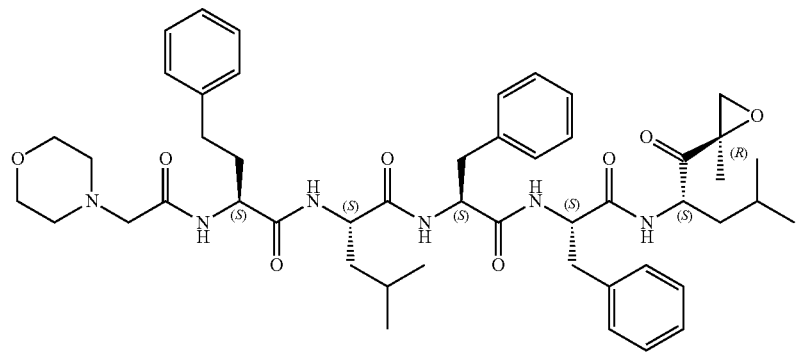

21

(S)-4-methyl-N—((S)-1-(((S)-1-(((S)-4-methyl-1-((R)-2-methyloxiran-2-yl)-1-oxopentan-2-yl)amino)-1-oxo-3-phenylpropan-2-yl)amino)-1-oxo-3-phenylpropan-2-yl)-2-((S)-2-(2-morpholinoacetamido)-4-phenylbutanamido)pentanamide

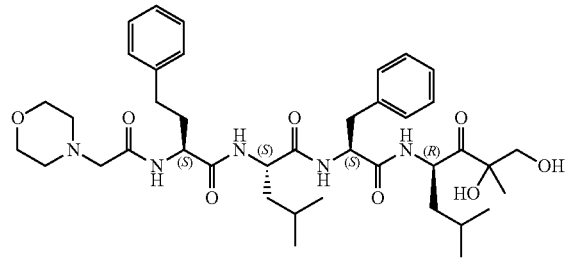

22

4-((4S,7S,10s, 13R)-10-benzyl-7-isobutyl-15-methyl-13-(2-methyloxirane-2-carbonyl)-2,5,8,11-tetraoxo-4-phenethyl-3,6,9,12-tetraazahexadecyl) morpholine 4-oxide

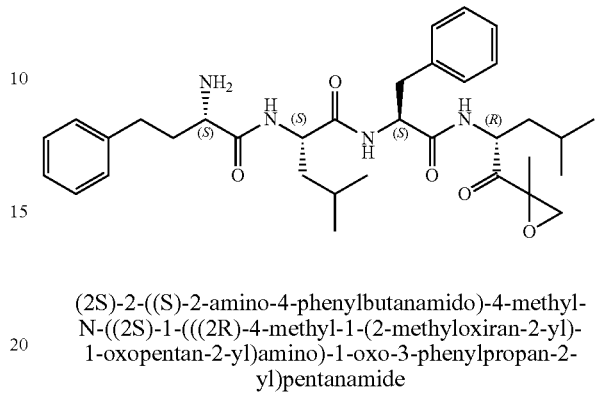

(2S)-2-((S)-2-amino-4-phenylbutanamido)-4-methyl-N-((2S)-1-(((2R)-4-methyl-1-(2-methyloxiran-2-yl)-1-oxopentan-2-yl)amino)-1-oxo-3-phenylpropan-2-yl)pentanamide

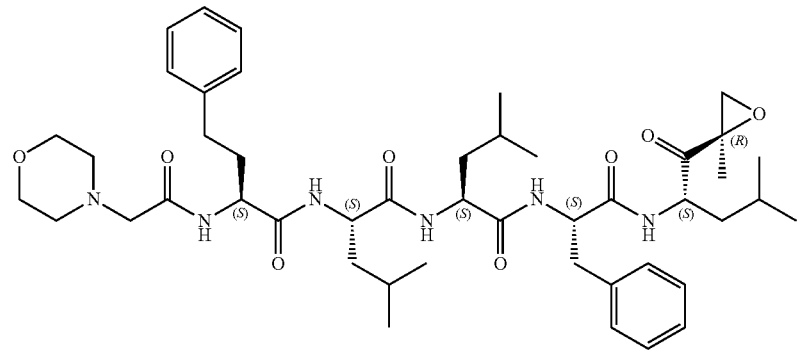

(2S)—N-((2S)-1-(((4R)-(4)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido) pentanamide (S)-4-methyl-N—((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2-((S)-2-(2-morpholinoacetamido)-4-phenylbutanamido)pentanamide

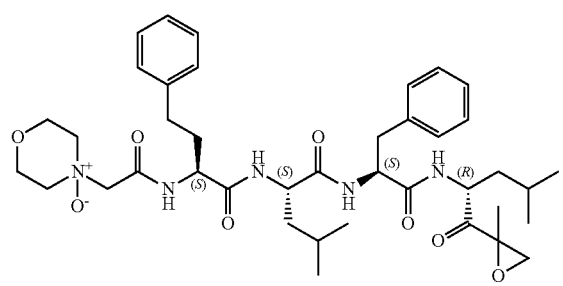

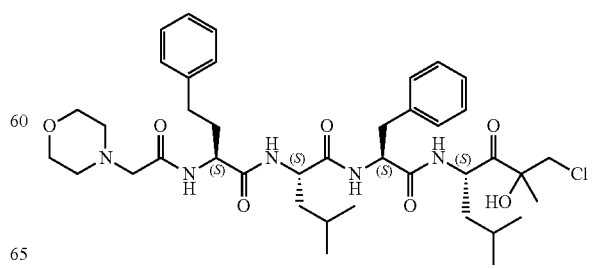

| 23 | 24 |
|---|---|
| (2S)—N-((2S)-1-(((4S)-1-chloro-2-hydroxy-2,6-dimethyl-3-oxoheptan-4-yl)amino)-1-oxo-3-phenyl-propan-2-yl)-4-methyl-2-((S)-2-(2-morpholinoacet-amido)-4-phenylbutanamido) pentanamide | (R)-4-methyl-N—((R)-1-(((S)-4-methyl-1-((R)-2-methyloxiran-2-yl)-1-oxopentan-2-yl)amino)-1-oxo-3-phenylpropan-2-yl)-2-((R)-2-(2-morpholinoacet-amido)-4-phenylbutanamido)pentanamide(R,R,R,S,R-Isomer) |

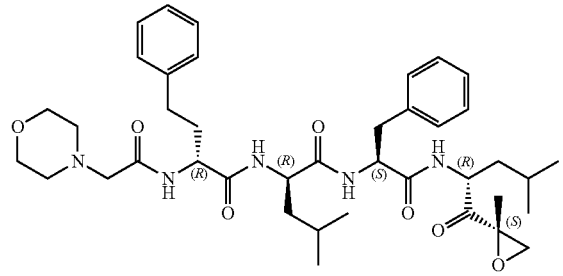

(R)-4-methyl-N—((S)-1-(((R)-4-methyl-1-((S)-2-methyloxiran-2-yl)-1-oxopentan-2-yl)amino)-1-oxo-3-phenylpropan-2-yl)-2-((R)-2-(2-morpholinoacet-amido)-4-phenylbutanamido)pentanamide (R)-4-methyl-N—((R)-1-(((S)-4-methyl-1-((S)-2-methyloxiran-2-yl)-1-oxopentan-2-yl)amino)-1-oxo-3-phenylpropan-2-yl)-2-((R)-2-(2-morpholinoacet-amido)-4-phenylbutanamido)pentanamide(R,R,R,S,S-Isomer)

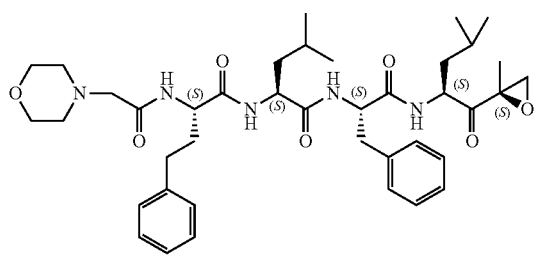

(S)-4-methyl-N—((S)-1-(((S)-4-methyl-1-((S)-2-methyloxiran-2-yl)-1-oxopentan-2-yl)amino)-1-oxo-3-phenylpropan-2-yl)-2-((S)-2-(2-morpholinoacet-amido)-4-phenylbutanamido)pentanamide (S,S,S,S,S-Isomer)

(S)-4-methyl-N—((S)-1-(((R)-4-methyl-1-((S)-2-methyloxiran-2-yl)-1-oxopentan-2-yl)amino)-1-oxo-3-phenylpropan-2-yl)-2-((S)-2-(2-morpholinoacet-amido)-4-phenylbutanamido)pentanamide (S,S,S,R,S-Isomer)

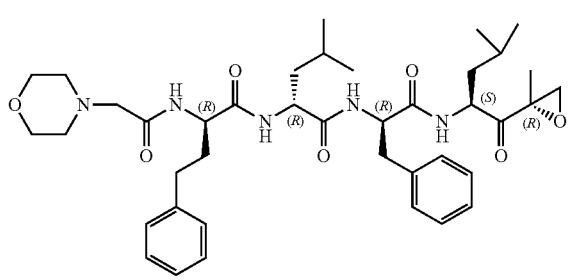
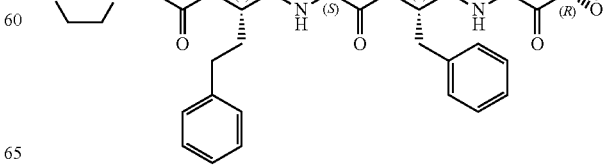

| 25 | 26 |
|---|---|
| (S)-4-methyl-N—((S)-1-(((R)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,S,S,R,R-Isomer) | (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide (R,S,S,S,R-Isomer) |

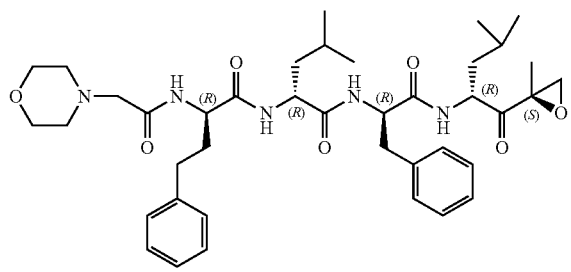 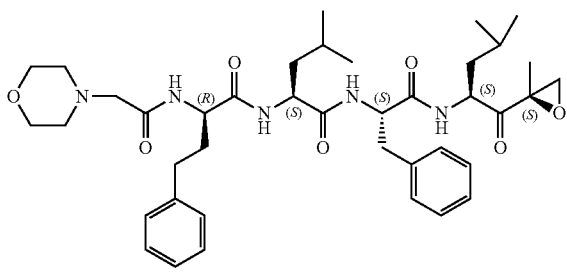

| | |
|---|---|
| ((R)-4-methyl-N—((R)-1-(((R)-4-methyl-1-((S)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R,R,R,R,S-Isomer) | (S)-4-methyl-N—((S)-1-(((S)-4-methyl-1-((S)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide (R,S,S,S,S-Isomer) |

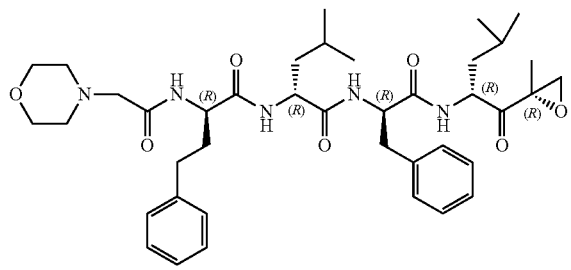 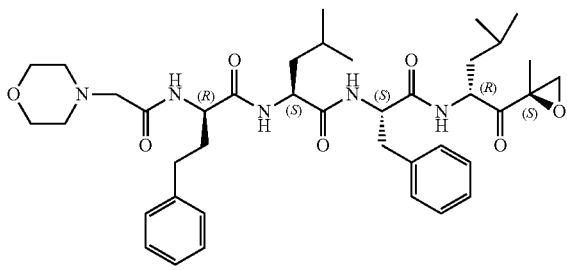

| | |
|---|---|
| (R)-4-methyl-N—((R)-1-(((R)-4-methyl-1-((R)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R,R,R,R,R-Isomer) | (S)-4-methyl-N—((S)-1-(((R)-4-methyl-1-((S)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide (R,S,S,R,S-Isomer) |

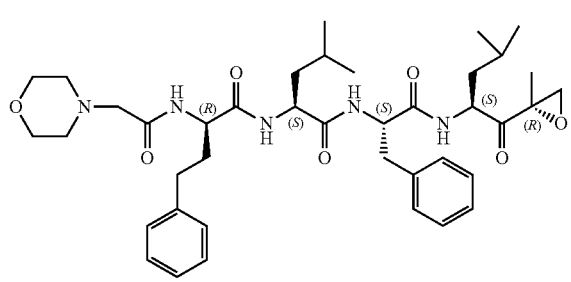 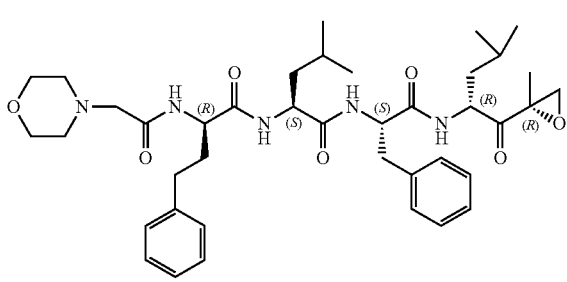

27

(S)-4-methyl-N—((S)-1-(((R)-4-methyl-1-((R)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R,S,S,R,R-Isomer)

28

(R)-4-methyl-N—((S)-4-methyl-1-((S)-2-methyloxiran-2-yl)-1-oxopentan 2-yl)amino-1-oxo-3-phenylpropan-2-yl)-2-((S)-2-(2-morpholinoacetamido)-4-phenylbutanamido)pentanamide (S,R,S,S,S-Isomer)

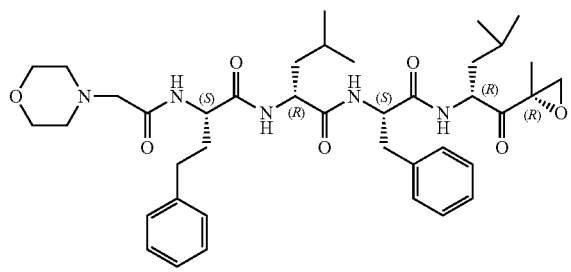
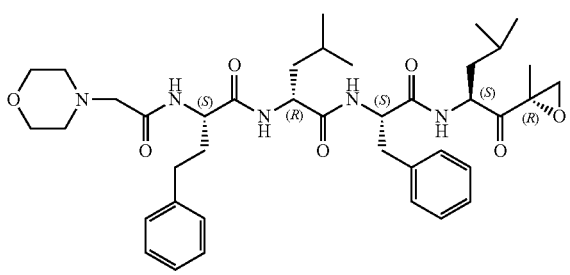

(R)-4-methyl-N—((S)-1-(((R)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,S,R,R-Isomer)

(R)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,S,S,R-Isomer)

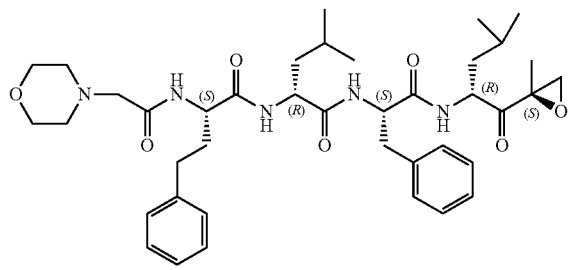
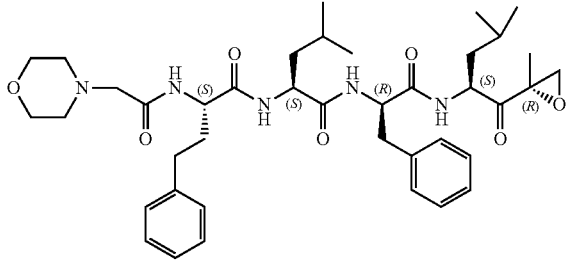

(R)-4-methyl-N—((S)-1-(((R)-4-methyl-1-((S)-2-methyl oxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,S,R,S-Isomer)

(S)-4-methyl-N—((R)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,S,R,S,R-Isomer)

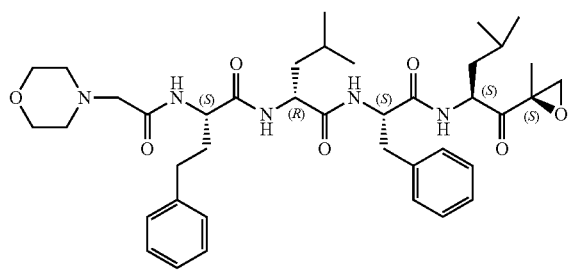
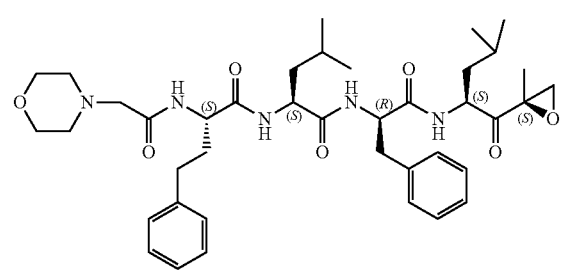

29

(S)-4-methyl-N—((R)-1-(((S)-4-methyl-1-((S)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (S,S,R,S,S-Isomer)

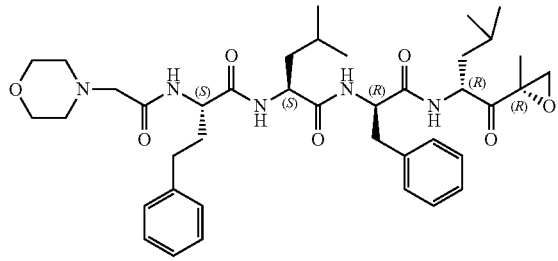

(S)-4-methyl-N—((R)-1-(((R)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,S,R,R,R-Isomer)

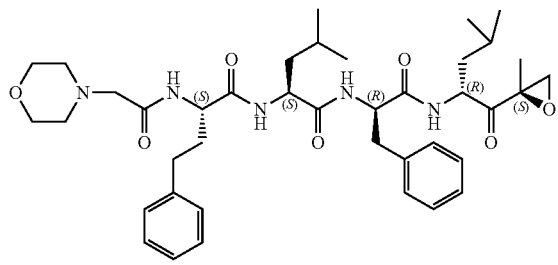

(S)-4-methyl-N—((R)-1-(((R)-4-methyl-1-((S)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,S,R,R,S-Isomer)

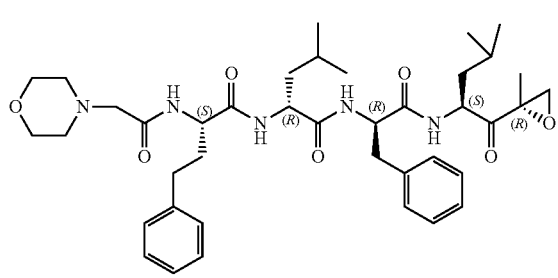

30

(R)-4-methyl-N—((R)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,R,S,R-Isomer)

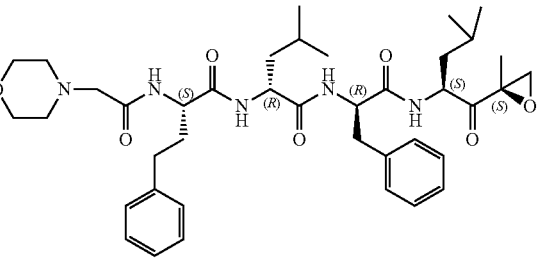

(R)-4-methyl-N—((R)-1-(((S)-4-methyl-1-((S)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,R,S,S-Isomer)

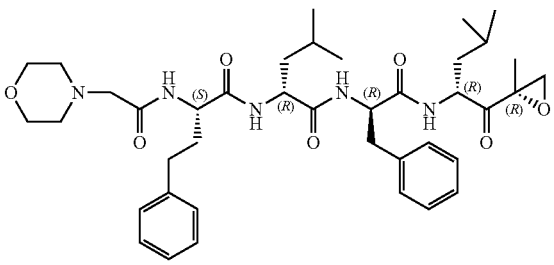

(R)-4-methyl-N—((R)-1-(((R)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,R,R,R-Isomer)

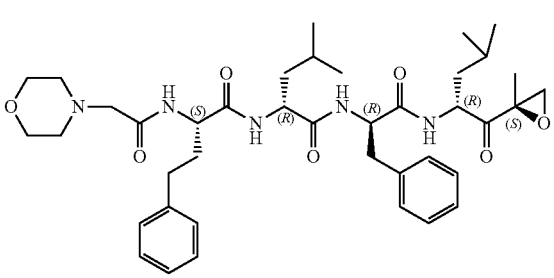

31

(R)-4-methyl-N—((R)-1-(((R)-4-methyl-1-((S)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide(S,R,R,R,S-Isomer)

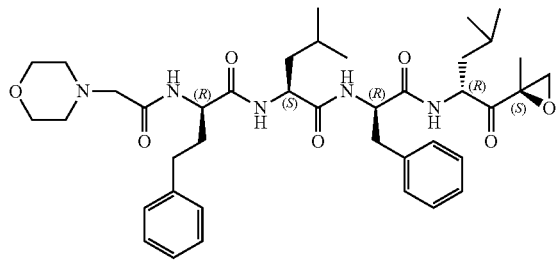

(S)-4-methyl-N—((R)-1-(((R)-4-methyl-1-((S)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R,S,R,R,S-Isomer)

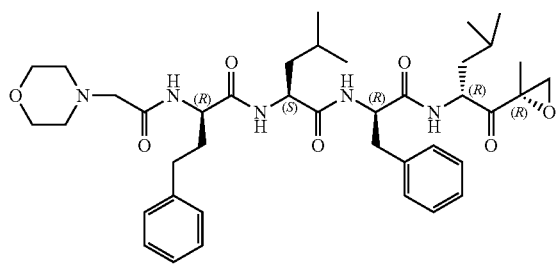

(S)-4-methyl-N—((R)-1-(((R)-4-methyl-1-((R)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R,S,R,R,R-Isomer)

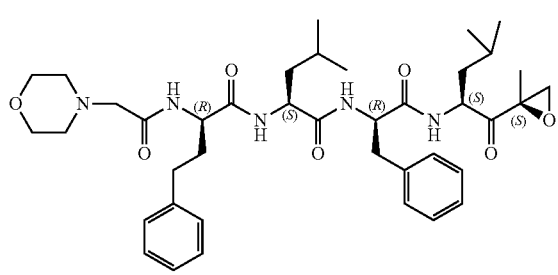

32

(S)-4-methyl-N—((R)-1-(((S)-4-methyl-1-((S)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide (R,S,R,S,S-Isomer)

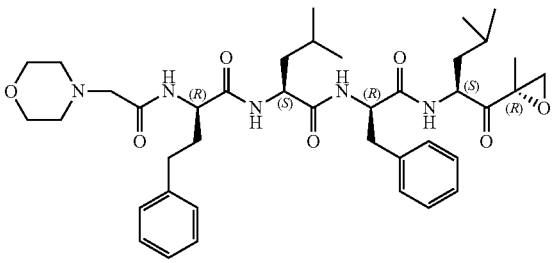

(S)-4-methyl-N—((R)-1-(((S)-4-methyl-1-((R)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R,S,R,S,R-Isomer)

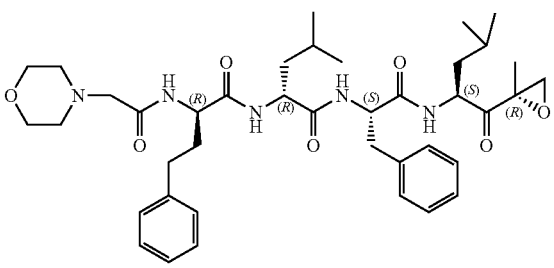

(R)-4-methyl-N—((S)-1-(((S)-4-methyl-1-((R)-2-methyloxiran-2-yl)-1-oxopentan-2-yl)amino)-1-oxo-3-phenylpropan-2-yl)-2-((R)-2-(2-morpholinoacetamido)-4-phenylbutanamido)pentanamide(R, R,S,S,R-Isomer)

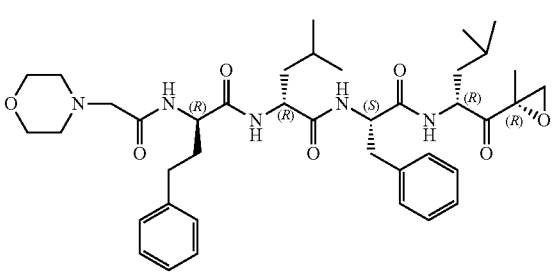

(R)-4-methyl-N—((S)-1-(((R)-4-methyl-1-((R)-2-methyloxiran-2-yl)-1-oxopentan-2-yl)amino)-1-oxo-3-phenylpropan-2-yl)-2-((R)-2-(2-morpholinoacet-amido)-4-phenylbutanamido)pentanamide(R,R,S,R,R-Isomer)

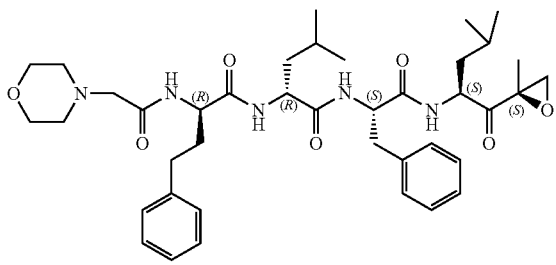

(R)-4-methyl-N—((S)-1-(((S)-4-methyl-1-((S)-2-methyloxiran-2-yl)-1-oxopentan-2-yl)amino)-1-oxo-3-phenylpropan-2-yl)-2-((R)-2-(2-morpholinoacet-amido)-4-phenylbutanamido)pentanamide (R,R,S,S,S-Isomer)

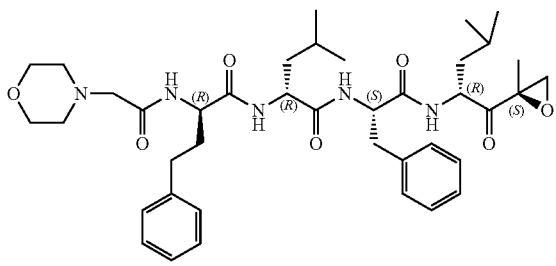

(R)-4-methyl-N—((S)-1-(((R)-4-methyl-1-((S)-2-methyloxiran-2-yl)-1-oxopentan-2-yl)amino)-1-oxo-3-phenylpropan-2-yl)-2-((R)-2-(2-morpholinoacet-amido)-4-phenylbutanamido)pentanamide(R,R,S,R,S-Isomer)

The possible impurities mentioned above are found to be less than 0.15% in the carfilzomib produced according to the processes of the present application.

Carfilzomib and its impurities can be analyzed using high performance liquid chromatography (HPLC), such as with a liquid chromatograph equipped with variable wavelength UV-detector and the method described below:

| Column | YMC-Pack ODS-A 150 × 4.6 mm, 3.0 μm |
| --- | --- |
| Wavelength | 210 nm |
| Flow rate | 0.9 mL/minute |
| Temperature | 25° C. |
| Concentration | 2 mg/mL |
| Injection volume | 10 μL |
| Diluent | Water:Acetonitrile = 2:8 (v/v) |
| Elution | Gradient |

Mobile phase-A: Mix solution-A and solution-B in the ratio of 800:200.
Mobile phase-B: Mix solution-A and solution-B in the ratio of 200:800.
Solution-A: 1.36 g of $KH_2PO_4$ dissolved in 1000 mL water and pH adjusted to 5.5 with potassium hydroxide.
Solution-B: Acetonitrile:Methanol in the ratio of 900:1100.

| Gradient program: | | |
| --- | --- | --- |
| Time | % Mobile phase-A | % Mobile phase-B |
| 0.0 | 50 | 50 |
| 3 | 50 | 50 |
| 20 | 20 | 80 |
| 40 | 20 | 80 |
| 50 | 15 | 85 |
| 60 | 5 | 95 |
| 65 | 5 | 95 |
| 70 | 0 | 100 |
| 90 | 0 | 100 |
| 91 | 50 | 50 |
| 100 | 50 | 50 |

In an aspect, the present application provides pharmaceutical formulations comprising amorphous form of carfilzomib, together with one or more pharmaceutically acceptable excipients. Amorphous form of carfilzomib together with one or more pharmaceutically acceptable excipients of the present application may be formulated as: solid oral dosage forms such as, but not limited to, powders, granules, pellets, tablets, or capsules; liquid oral dosage forms such as, but not limited to, syrups, suspensions, dispersions, or emulsions; or injectable preparations such as, but not limited to, solutions, dispersions, or freeze dried compositions. Formulations may be in the forms of immediate release, delayed release, or modified release. Further, immediate release compositions may be conventional, dispersible, chewable, mouth dissolving, or flash melt preparations, or modified release compositions that may comprise hydrophilic or hydrophobic, or combinations of hydrophilic and hydrophobic, release rate controlling substances to form matrix or reservoir or combination of matrix and reservoir systems. The compositions may be prepared using techniques such as direct blending, dry granulation, wet granulation, or extrusion and spheronization. Compositions may be presented as uncoated, film coated, sugar coated, powder coated, enteric coated, or modified release coated. Compositions of the present application may further comprise one or more pharmaceutically acceptable excipients.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar, or the like; binders such as acacia, guar gum, tragacanth, gelatin, polyvinylpyrrolidones, hydroxypropyl celluloses, hydroxypropyl methyl celluloses, pregelatinized starches, or the like; disintegrants such as starches, sodium starch glycolate, pregelatinized starches, crospovidones, croscarmellose sodium, colloidal silicon dioxide, or the like; lubricants such as stearic acid, magnesium stearate, zinc stearate, or the like; glidants such as colloidal silicon dioxide or the like; solubility or wetting enhancers such as anionic or cationic or neutral surfactants; complex forming agents such as various grades of cyclodextrins or resins; release rate controlling agents such as hydroxypropyl celluloses, hydroxymethyl celluloses, hydroxypropyl methylcelluloses, ethylcelluloses, methylcelluloses, various grades of methyl methacrylates, waxes, or the like. Other pharmaceutically acceptable excipients that are of use include, but are not limited to, film formers, plasticizers, colorants, flavoring agents, sweeteners, viscosity enhancers, preservatives, antioxidants, or the like.

Carfilzomib amorphous form obtained according to the process of the present application is stable at 2-8° C. for extended periods, i.e., more than 3 month.

DEFINITIONS

The following definitions are used in connection with the present invention unless the context indicates otherwise. The term "amorphous" refers to a solid lacking any long-range translational orientation symmetry that characterizes crystalline structures although, it may have short range molecular order similar to a crystalline solid.

The term "anti-solvent" refers to a liquid that, when combined with a solution of carfilzomib, reduces solubility of the carfilzomib in the solution, causing crystallization or precipitation in some instances spontaneously, and in other instances with additional steps, such as seeding, cooling, scratching and/or concentrating.

Celite is flux-calcined diatomaceous earth. Hyflow is flux-calcined diatomaceous earth treated with sodium carbonate.

An "alcohol solvent" is an organic solvent containing a carbon bound to a hydroxyl group. "Alcoholic solvents" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, $C_{1-6}$ alcohols, or the like. A "hydrocarbon solvent" refers to a liquid, non-aromatic, hydrocarbon, which may be linear, branched, or cyclic. It is capable of dissolving a solute to form a uniformly dispersed solution. Examples of a hydrocarbon solvents include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, Examples of aromatic hydrocarbon solvents include, but are not limited to benzene, toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, or mixtures thereof.

An "ester solvent" is an organic solvent containing a carboxyl group —(C=O)—O-bonded to two other carbon atoms. "Ester solvents" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, $C_{3-6}$ esters, or the like.

A "halogenated hydrocarbon solvent" is an organic solvent containing a carbon bound to a halogen. "Halogenated hydrocarbon solvents" include, but are not limited to, dichloromethane, 1,2-dichloroethane, trichloroethylene, perchloroethylene, 1,1,1-trichloroethane, 1,1,2-trichloroethane, chloroform, carbon tetrachloride, or the like.

A "ketone solvent" is an organic solvent containing a carbonyl group —(C=O)— bonded to two other carbon atoms. "Ketone solvents" include, but are not limited to, acetone, ethyl methyl ketone, diethyl ketone, methyl isobutyl ketone, $C_{3-6}$ ketones, 4-methyl-pentane-2-one or the like.

A "nitrile solvent" is an organic solvent containing a cyano —(C≡N) bonded to another carbon atom. "Nitrile solvents" include, but are not limited to, acetonitrile, propionitrile, $C_{2-6}$ nitriles, or the like.

A "polar aprotic solvent" has a dielectric constant greater than 15 and is at least one selected from the group consisting of amide-based organic solvents, such as N,N-dimethylformamide (DMF), N,N-dimethylacetamide (DMA), N-methylpyrrolidone (NMP), formamide, acetamide, propanamide, hexamethyl phosphoramide (HMPA), and hexamethyl phosphorus triamide (HMPT); nitro-based organic solvents, such as nitromethane, nitroethane, nitropropane, and nitrobenzene; pyridine-based organic solvents, such as pyridine and picoline; sulfone-based solvents, such as dimethylsulfone, diethylsulfone, diisopropylsulfone, 2-methylsulfolane, 3-methylsulfolane, 2,4-dimethylsulfolane, 3,4-dimethylsulfolane, 3-sulfolene, and sulfolane; and sulfoxide-based solvents such as dimethylsulfoxide (DMSO).

An "ether solvent" is an organic solvent containing an oxygen atom —O— bonded to two other carbon atoms. "Ether solvents" include, but are not limited to, diethyl ether, diisopropyl ether, methyl t-butyl ether, glyme, diglyme, tetrahydrofuran (THF), 2-methyltetrahydrofuran, 1,4-dioxane, dibutyl ether, dimethylfuran, 2-methoxyethanol, 2-ethoxyethanol, anisole, $C_{2-6}$ ethers, or the like.

An "inorganic base" is sodium hydroxide, potassium hydroxide, sodium carbonate, or potassium carbonate, sodium bicarbonate or potassium bicarbonate.

An "organic base" is an organic compound, which acts as a base. Examples of such bases include, but are not limited to, triethylamine, diisopropylamine, Hunig's base, DABCO, triethanolamine, tributylamine, pyridine, lutidine, 4-dimethylamino pyridine (DMAP), N-methylpyrrolidine, diethanolamine, 4-methylmorpholine, dimethylethanolamine, tetramethylguanidine, morpholine, imidazole, 2-methylimidazole, 4-methylimidazole, tetramethylammonium hydroxide, tetraethylammonium hydroxide, N-methyl-1,5,9-triazabicyclo[4.4.0] decene, 1,8-diazabicyclo[5.4.0]undec-7-ene, dicyclohexylamine, and picoline.

As used herein, the term "co-crystal" refers to a crystal complex composed of at least two neutral molecules bound together in a crystal lattice by non-covalent interactions. The term "co-crystal" also can be referred as adduct.

Certain specific aspects and embodiments of the present invention will be explained in more detail with reference to the following examples, which are provided for purposes of illustration only and should not be construed as limiting the scope of the present invention in any manner.

EXAMPLES

Example 1: Preparation of Amorphous Form of Carfilzomib

Carfilzomib (500 mg) and methanol (10 mL) were charged into a round bottom flask at 28° C. The reaction mass was stirred to dissolve carfilzomib completely. The obtained solution was filtered to obtain a clear solution. Water (50 mL) was charged into a flask. The above obtained clear solution was added to water under stirring at 28° C. The resulting slurry was filtered. The solid product was obtained as amorphous carfilzomib. Yield: 58.2%; Purity by HPLC: 98.03%

Example 2: Preparation of Amorphous Form of Carfilzomib

Carfilzomib (2 g) and methanol (35 mL) were charged into a round bottom flask at 28° C. The reaction mass was stirred to dissolve carfilzomib completely. The obtained solution was filtered to obtain a clear solution. Water (35 mL) was charged into a flask. The above obtained clear solution was added to water under stirring at 28° C. The resulting slurry was filtered. The solid product was obtained as amorphous carfilzomib. Yield: 55.65%; Purity by HPLC: 98.47%

Example 3: Preparation of Amorphous Form of Carfilzomib

Carfilzomib (200 mg) and dichloromethane (1 mL) were charged into a round bottom flask at 28° C. The reaction mass was stirred to dissolve carfilzomib completely. The obtained solution was filtered to obtain a clear solution. n-heptane (4 mL) was charged into a flask. The above obtained clear solution was added to n-heptane under stirring at 28° C. The resulting slurry was filtered. The solid product was obtained as amorphous carfilzomib. Wet weight: 140 mg

Example 4: Preparation of Amorphous Form of Carfilzomib

Carfilzomib (700 mg) and dichloromethane (2 mL) were charged into a round bottom flask at 28° C. The reaction mass was stirred to dissolve carfilzomib completely. The obtained solution was filtered to obtain a clear solution. n-heptane (10 mL) was charged into a flask under stirring at 28° C. The clear solution was added to n-heptane. The resulting slurry was filtered. The solid product was obtained as amorphous carfilzomib. Wet weight: 460 mg; Purity by HPLC: 98.22%

Example 5: Preparation of Amorphous Form of Carfilzomib

Carfilzomib (1 g) and methanol (17 mL) were charged into a round bottom flask at 28° C. The reaction mass was stirred to dissolve carfilzomib completely. The obtained solution was filtered to obtain a clear solution. The resulting solution was evaporated completely in buchi rotavapor at 45° C. under reduced pressure to obtained title compound. Wet weight: 0.5 g; Purity by HPLC: 98.15%

Example 6: Preparation of Carfilzomib 230-400 mesh silicagel (100 g) in n-hexane (250 mL) was loaded into column. Carfilzomib crude (5 g) was dissolved in dichloromethane (15 mL) and loaded into column. Carfilzomib was eluted with ethyl acetate (1000 mL) and n-hexane (250 mL). The resulting fractions 1, 2, 3 and 4 were evaporated completely in buchi rotavapor at 30° C. under reduced pressure to obtained pure title compound from fraction 2. Wet weight: 3.9 g; Purity by HPLC: 98.02%

Example 7: Preparation of Co-Crystal of Carfilzomib with Maleic Acid

Carfilzomib (1 g) and maleic acid (0.161 g) were dissolved in THF (7.5 mL) and acetonitrile (5 mL). The solution was then stirred for 2 hours at 28° C., at which time a white precipitate formed. The flask was then cooled to −1° C. and stirred 2 hours. The solids were filtered and washed with acetonitrile (10 mL) to give 1.03 g of the co-crystal of carfilzomib with maleic acid.

Example 8: Preparation of Carfilzomib

Co-crystal of carfilzomib with maleic acid (0.5 g) and methanol (10 mL) were charged into a round bottom flask at 27° C. 1% $NaHCO_3$ (5 mL) solution added to the reaction mass. The solution was then stirred for 7 minutes at 27° C. Water (30 mL) was charged into another round bottom flask at 27° C. The above resulting clear carfilzomib solution was added to water at 27° C. The solution was then stirred for 50 minutes at 27° C. The solids were filtered and washed with water (10 mL) to give 350 mg of carfilzomib.

Example 9: Preparation of Co-Crystal of Carfilzomib with Maleic Acid

Carfilzomib (2 g) and maleic acid (0.322 g) were dissolved in THF (15 mL) and acetonitrile (10 mL). The solution was then stirred for 10 minutes at 26° C. THF (5 mL) acetonitrile (10 mL) were charged and stirred for 2 hours at 26° C. The solids were filtered and washed with acetonitrile (20 mL) to give 1.75 g of the co-crystal of carfilzomib with maleic acid.

Example 10: Preparation of Carfilzomib

Co-crystal of carfilzomib with maleic acid (0.5 g) and methanol (10 mL) were charged into a round bottom flask at 27° C. 1% $NaHCO_3$ (5 mL) solution added to the reaction mass. The solution was then stirred for 5 minutes at 27° C. Water (30 mL) was charged into another round bottom flask at 27° C. The above resulting clear carfilzomib solution was added to water at 27° C. The solution was then stirred for 50 minutes at 27° C. The solids were filtered and washed with water (5 mL) to give 352 mg of carfilzomib.

Example 11: Preparation of Carfilzomib

Co-crystal of carfilzomib with maleic acid (0.5 g) and methanol (10 mL) were charged into a round bottom flask at 25° C. 13.7 equivalents of $NaHCO_3$ solution added to the reaction mass. The solution was then stirred for 2 hours at 23° C. The solids were filtered and washed with water (10 mL) to give 360 mg of carfilzomib.

Example 12: Preparation of Amorphous Form of Carfilzomib

Carfilzomib (20 g) and methanol (350 mL) were charged into a round bottom flask at 26° C. The reaction mass was stirred to dissolve carfilzomib completely. The obtained solution was filtered to obtain a clear solution. Water (350 mL) was charged into a flask. The above obtained clear solution was added to water under stirring at 26° C. The reaction mass was stirred for 20 minutes at 26° C. The resulting slurry was filtered and washed with water (200 mL). The solid product was obtained as amorphous carfilzomib. Wet weight: 24 gm

Example 13

Preparation of (S)-Methyl 2-((S)-2-((S)-2-Amino-4-phenylbutanamido)-4-methylpentanamido)-3-phenylpropanoate hydrochloride. (S)-2-((tert-butoxycarbonyl)amino)-4-phenylbutanoic acid (10 g), TFA salt of (S)-methyl 2-((S)-2-amino-4-methylpentanamido)-3-phenylpropanoate (14.55 g), ethyl acetate (200 mL), 1H-benzo[d][1,2,3]triazol-1-ol hydrate (5.48 g), 3-(((ethylimino)methylene)amino)-N,N- dimethylpropan-1-aminium chloride (13.73 g) and N-ethyl-N-isopropylpropan-2-amine (6.94 g) were charged into a round bottom flask at 31° C. The reaction mass was stirred for 11 hours. Water (100 mL) was added to the reaction mass at 29° C. The organic and aqueous layers were separated. The organic layer was washed with aqueous HCl solution (100 mL), aqueous NaHCO$_3$ (100 mL) and NaCl solution (100 mL). The reaction mass was evaporated at 50° C. Ethyl acetate (100 mL) was added to the reaction mass. The reaction mass was evaporated at 50° C. Methanol (100 mL) was added to the reaction mass. The reaction mass was evaporated under vacuum at 50° C. Methanolic HCl (150 mL) was added to the residue. The reaction mass was stirred for 1 hour at 30° C. Diisopropyl ether (150 mL) was added to the reaction mass. The reaction mass was stirred for 1 hour at 30° C. The precipitated solid was filtered and washed with diisopropyl ether (100 mL). The solid was dried under vacuum at 28° C. for 1 hour. Product weight: 13.5 g; purity by HPLC: 99.26%.

Example 14

Preparation of lithium (S)-2-((S)-4-methyl-2-((S)-2-(2-morpholinoacetamido)-4-phenylbutanamido)pentanamido)-3-phenylpropanoate. (S)-methyl 2-((S)-2-((S)-2-amino-4-phenylbutanamido)-4-methylpentanamido)-3-phenylpropanoate hydrochloride (250 g) and DMF (1.5 l) were charged into a round bottom flask at 24° C. The reaction mass was cooled to 4° C. HCl salt of morpholine aceticacid (144 g), EDC.HCl (196 g), DMAP (62.3 g) and DIEPA were added to the reaction mass at 4° C. The reaction mass was stirred at 10° C. for 15 minutes. The reaction mass was stirred at 16° C. for 4 hours. Ethyl acetate (2.5 l) and water (5 L) were added to the reaction mass at 20° C. The organic and aqueous layers were separated. The aqueous layer was extracted with ethyl acetate (2.5 L). The combined extracts were washed with 0.15 N HCl solution (1.25 L), 7% NaHCO$_3$ solution (2.5 L) and 10% NaCl solution (2.5 L). The reaction mass was evaporated under vacuum at 46° C. Acetonitrile (2.5 L) was added to the reaction mass. The reaction mass was evaporated at 46° C. Acetonitrile (3.75 L) was added to the reaction mass at 23° C. The reaction mass was cooled to 11° C. LiOH solution (62.4 g in 0.25 L of water). The reaction mass was stirred for 6 hours at 7° C. Acetonitrile (4.5 L) was added to the reaction mass at 10° C. The reaction mass was stirred for 1 hour at 12° C. The precipitated solid was filtered. The solid was dried under vacuum at 28° C. for 1 hour. Water (2.5 L) was added to the above obtained solid at 21° C. The reaction mass was stirred for 1 hour at 21° C. The precipitated solid was filtered and washed with acetonitrile (1.25 L). The solid was dried under vacuum at 50° C. for 20 hours.

Example 15: Preparation of Carfilzomib

Lithium (S)-2-((S)-4-methyl-2-((S)-2-(2-morpholinoacetamido)-4-phenylbutanamido)pentanamido)-3-phenylpropanoate (10 g) and DMF were charged into a round bottom flask under nitrogen atmosphere at 24° C. The reaction mass was cooled to 2° C. (S)-2-amino-4-methyl-1-((R)-2-methyloxiran-2-yl)pentan-1-one (5.87 g) and 2-(3H-[1,2,3]triazol[4,5-b]pyridine-3-yl)1,1,3,3-tetramethylisouronium hexafluorophosphate (8.07 g) were added to the reaction mass at 2° C. The reaction mass was stirred for 3 hours at 5° C. Ethyl acetate (200 mL) and water (100 mL) were added to the reaction mass at 8° C. The reaction mass was stirred for 10 minutes at 8° C. The organic and aqueous layers were separated. The aqueous layer was extracted with ethyl acetate (100 mL). The combined extracts were washed with water (10 mL). Extracts were charged in to a round bottom flask. Maleic acid solution (0.242 g in 20 mL of ethyl acetate) was added to the reaction mass. The reaction mass was stirred for 2 hours at 25° C. The precipitated solid was filtered and washed with ethylacetate (200 mL). The solid was dried under vacuum at 30° C. for 31 hours. Purity by HPLC: 99.03%.

Example 16: Preparation of Carfilzomib

Co-crystal of carfilzomib with maleic acid (2 g), DMF (4 mL) and acetonitrile (60 mL) were charged into a round bottom flask at 24° C. The reaction mass temperature was raised to 66° C. The reaction mass was stirred for 1 hour at 66° C. The reaction mass was cooled to 23° C. The reaction mass was stirred for 2 hours at 23° C. The precipitated solid was filtered and washed with acetonitrile (20 mL). The solid was dried under vacuum at 23° C. for 1 hour. The above obtained solid was dissolved in methanol (20 mL). This methanolic solution was added to the NaHCO$_3$ solution (1.95 g in 100 mL of water) at 4° C. The reaction mass was stirred for 2 hours at 2° C. The precipitated solid was filtered and washed with water (20 mL). The solid was dried under vacuum at 23° C. for 1 hour. The above obtained solid and water (50 mL) charged into a round bottom flask at 24° C. The reaction mass was stirred for 1 hour at 24° C. The precipitated solid was filtered and washed with water (20 mL). The solid was dried under vacuum at 23° C. for 1 hour. The above obtained solid was dissolved in methanol (20 mL) and filtered through micron filter. Water (120 mL) was charged into a round bottom flask at 24° C. The reaction mass was cooled to 3° C. Methanolic solution was added to the water at 3° C. for 30 minutes. The precipitated solid was filtered and washed with water (20 mL). The solid was dried under vacuum at 23° C. for 3 hours. The solid was further dried under vacuum at 30° C. for 9 hours.

Example 17: Preparation of Carfilzomib

Co-crystal of carfilzomib with maleic acid (1 g) and methanol (25 mL) were charged into a round bottom flask at 24° C. The reaction mass was stirred for 5 minutes and filtered through micron filter paper. Methanol filtrate was charged into automated reactor at 24° C. The reaction mass was cooled to 3° C. NaHCO$_3$ solution (2.51 g in 87.5 mL) added to the reaction mass at 3° C. The reaction mass was maintained for 5 hours at 3° C. The precipitated amorphous compound was filtered and washed with water (10 mL). The amorphous compound was dried under vacuum at 30° C. for 10 hours. Product weight: 0.65 g; purity by HPLC: 99.02%.

The invention claimed is:

1. A co-crystal of carfilzomib with maleic acid.

2. The co-crystal of carfilzomib with maleic acid of claim 1 characterized by peaks in the powder x-ray diffraction pattern at 2θ values of 7.4±0.2, 18.1±0.2 and 18.7±0.2.

3. The co-crystal of carfilzomib with maleic acid of claim 1 further characterized by peaks in the powder x-ray diffraction pattern at 2θ values of 4.5±0.2, 9.2±0.2, 16.3±0.2, 20.2±0.2, 20.6±0.2, 21.7±0.2 and 22.3±0.2.

4. The co-crystal of carfilzomib with maleic acid of claim 1 having powder x-ray diffraction pattern as shown in FIG. 2.

5. The co-crystal of carfilzomib with maleic acid of claim 1 characterized by unit cell parameters substantially equal to the following cell dimensions:

a=19.790(5) Å
b=9.807(8) Å
c=12.067(7) Å
α=90°
β=98.117(9)°
γ=90°
Space group=P2$_1$
Molecules/asymmetric unit=1.

6. A process for the preparation of the co-crystal of carfilzomib with maleic acid of claim 1, wherein the process comprises:
   a) preparing a solution of carfilzomib in a solvent selected from ethyl acetate, DMF, water or mixtures thereof;
   b) adding maleic acid;
   c) isolating co-crystal of carfilzomib with maleic acid.

7. A process for the preparation of pure carfilzomib comprising:
   a) preparing co-crystal of carfilzomib with maleic acid in solvent;
   b) optionally, purifying co-crystal of carfilzomib with maleic acid using solvent;
   c) converting the co-crystal of carfilzomib with maleic acid to carfilzomib free-base using base;
   d) optionally, purifying carfilzomib with solvent.

8. The process according to claim 7 wherein the solvent is selected from ester solvents; polar aprotic solvents; nitrile solvents; alcohol solvents; halogenated hydrocarbon solvents; ketone solvents; water or mixtures thereof.

9. The process according to claim 8 wherein the solvent is selected from ethyl acetate, DMF, acetonitrile, methanol, water or mixtures thereof.

10. The process according to claim 7 wherein the base is selected form inorganic and organic bases.

11. The process according to claim 10 wherein the base is selected from sodium hydroxide, potassium hydroxide, sodium carbonate, potassium carbonate, sodium bicarbonate, potassium bicarbonate, triethylamine, diisopropylethylamine, diisopropylamine, N-methyl morpholine and pyridine.

12. A process for the preparation of pure carfilzomib comprising:
   a) treating lithium ((S)-2-(2-morpholinoacetamido)-4-phenylbutanoyl)-L-leucyl-L-phenylalaninate with (S)-2-amino-4-methyl-1-((R)-2-methyloxiran-2-yl)pentan-1-one, adding maleic acid to provide co-crystal of carfilzomib with maleic acid;
   b) optionally, purifying the co-crystal of carfilzomib with maleic acid;
   c) converting the co-crystal of carfilzomib with maleic acid to Carfilzomib free-base;
   d) isolating the pure carfilzomib;
   e) optionally, further purifying carfilzomib.

13. The co-crystal of carfilzomib with maleic acid of claim 1 for use in the preparation of carfilzomib.

* * * * *